US009868988B2

(12) United States Patent
Suthanthiran

(10) Patent No.: US 9,868,988 B2
(45) Date of Patent: Jan. 16, 2018

(54) METHOD TO ASSESS HUMAN ALLOGRAFT STATUS FROM MICRORNA EXPRESSION LEVELS

(75) Inventor: Manikkam Suthanthiran, Scarsdale, NY (US)

(73) Assignee: Cornell University, Ithaca, NY (US)

(*) Notice: Subject to any disclaimer, the term of this patent is extended or adjusted under 35 U.S.C. 154(b) by 622 days.

(21) Appl. No.: 13/256,422

(22) PCT Filed: Mar. 15, 2010

(86) PCT No.: PCT/US2010/027361
§ 371 (c)(1),
(2), (4) Date: Nov. 22, 2011

(87) PCT Pub. No.: WO2010/105275
PCT Pub. Date: Sep. 16, 2010

(65) Prior Publication Data
US 2012/0101001 A1   Apr. 26, 2012

Related U.S. Application Data

(60) Provisional application No. 61/160,188, filed on Mar. 13, 2009.

(51) Int. Cl.
*C12Q 1/68* (2006.01)
(52) U.S. Cl.
CPC ..... *C12Q 1/6883* (2013.01); *C12Q 2600/158* (2013.01); *C12Q 2600/178* (2013.01)
(58) Field of Classification Search
None
See application file for complete search history.

(56) References Cited

U.S. PATENT DOCUMENTS

| | | | |
|---|---|---|---|
| 6,187,534 B1 | 2/2001 | Strom et al. | |
| 6,900,015 B2 | 5/2005 | Avihingsanon et al. | |
| 9,746,479 B2 | 8/2017 | Suthanthiran et al. | |
| 2001/0051344 A1* | 12/2001 | Shalon et al. | 435/6 |
| 2004/0053284 A1 | 3/2004 | Andrus et al. | |
| 2005/0175539 A1 | 8/2005 | Morishita et al. | |
| 2006/0088836 A1 | 4/2006 | Wohlgemuth et al. | |
| 2007/0010759 A1 | 1/2007 | Parsonnet et al. | |
| 2007/0031890 A1 | 2/2007 | Wohlgemuth et al. | |
| 2008/0131441 A1 | 6/2008 | Suthanthiran | |
| 2010/0303806 A1* | 12/2010 | Harvey | A01K 67/0275 424/132.1 |
| 2013/0012860 A1 | 1/2013 | Suthanthiran et al. | |

FOREIGN PATENT DOCUMENTS

| | | |
|---|---|---|
| CM | 1654637 A | 8/2005 |
| EP | 0534858 A1 | 3/1993 |
| WO | WO-2008/079303 A2 | 7/2008 |
| WO | WO-2010/105275 A2 | 9/2010 |
| WO | WO-2011/112719 A1 | 9/2011 |

OTHER PUBLICATIONS

Li et al., Noninvasive diagnosis of renal-allograft rejection by measurement of messenger RNA for perforin and granzyme B in urine; New England Journal of Medicine, vol. 344, No. 13, pp. 947-944, 2001.*
Kroese et al., Genetic tests and their evaluation: Can we answer the key questions?; Genetics in Medicine vo. 6, No. 6, pp. 475-480, 2004.*
Lucentini, Gene association studies typically wrong; The Scientist, vol. 18 No. 24, p. 20, 2004.*
Anglicheau et al., MicroRNA expression profiles predictive of human renal allograft status; PNAS, vol. 106, No. 13, pp. 5330-5335, 2009.*
"Chinese Application Serial No. 201080021368.6, Office Action mailed Oct. 23, 2013", (w/English Translation) 12 pgs.
"Chinese Application Serial No. 201080021368.6, Voluntary Amendment filed Jul. 18, 2013", (w/English Translation of Claims), 29 pgs.
"European Application Serial No. EP10751549.6, Amendment filed Oct. 12, 2011", 7 pgs.
"International Application Serial No. PCT/US10/27361, International Search Report mailed Nov. 4, 2010", 6 pgs.
"Chinese Application Serial No. 201080021368.6, Response filed Mar. 7, 2014 to Office Action mailed Oct. 23, 2013", 102 pgs.
"*Homo sapiens* miRNAs (1872 sequences)", [online], [retrieved on Feb. 25, 2014]. Retrieved from the Internet: <URL: http://www.mirbase.org/cgi-bin/mirna_summary.pl?org=hsa>, (2014), 48 pgs.
"International Application Serial No. PCT/US2010/027361, International Preliminary Report on Patentability mailed Feb. 27, 2014", 9 pgs.
"International Application Serial No. PCT/US2010/027361, Written Opinion mailed Nov. 4, 2010", 7 pgs.
"TaqMan® MicroRNA Assays and Arrays—Product Bulletin", © 2011 Life Technologies Corporation, (2011), 4 pgs.
Anglicheau, A., et al., "MicroRNA expression profiles predictive of human renal allograft status", *Proc. Natl. Acad. Sci. USA*, 106(13), (2009), 5330-5335.
Raymond, C. K., et al., "Simple, quantitative primer-extension PCR assay for direct monitoring of microRNAs and short-interfering RNAs", RNA, 11, (2005), 1737-1744.
Sui, W., et al., "Microarray analysis of MicroRNA expression in acute rejection after renal transplantation", *Transpl. Immunol.*, 19(1), (Apr. 2008), 81-85.
Dai et al., "Comprehensive analysis of microRNA expression patterns in renal biopsies of lupus nephritis patients," Rheumatol. Int., 29:749-754 (2009).

(Continued)

*Primary Examiner* — Addison D Ault
(74) *Attorney, Agent, or Firm* — Schwegman Lundberg & Woessner, P.A.

(57) ABSTRACT

The invention relates to, among other things, a method for assessing risk of organ rejection in a patient having a transplanted organ. The method includes measuring an amount of expression of a small non-coding marker RNA in a biological sample from the patient. The method further includes comparing the measured amount of expression of the small non-coding marker RNA in the patient to a reference amount of expression of the small non-coding marker RNA. In another aspect, the invention relates to kits for assessing risk of organ rejection in a patient having a transplanted organ.

14 Claims, 9 Drawing Sheets

(56) References Cited

OTHER PUBLICATIONS

D'Cruz et al., "Antibodies to endothelial cells in systemic lupus erythematosus: a potential marker for nephritis and vasculitis,"Clin. exp. Immunol., 85:254-261 (1991).
Ferry et al., "Anti-cell surface endothelial antibodies in sera from cardiac and kidney transplant recipients: association with chronic rejection," Transplant Immunology, 5:17-24 (1997).
Chan et al., "Expression of Chemokine and Fibrosing Factor Messenger RNA in the Urinary Sediment of Patients With Lupus Nephritis," Arthritis & Rheumatism, 50(9):2882-2890 (2004).
Grandaliano et al., "Monocyte chemotactic peptide-1 expression and monocyte infiltration in acute renal transplant rejection 1," Transplantation, 63(3):414-420 (1997).
miRNA entry M10000458 hsa-miR-148. miRBase (online) Apr. 2010 [retrieved on Jul. 30, 2010] Retrieved from the internal URL: <http://www.mirbase.org/cgi-bin/mirna_entry.pl?id=hsa-miR-142-5p>. Mature sequence.
Cobb et al., "A role for Dicer in immune regulation," The Journal of Experimental Medicine, 203(11):2519-2527 (2006).
Wu et al., "miRNA Profiling of Naive, Effector and Memory CD8 T Cells," PLoS, 2(10) e1020:1-11 (2007).
"U.S. Appl. No. 13/583,750, Final Office Action mailed Jul. 30, 2014", 17 pgs.
"U.S. Appl. No. 13/583,750, Non Final Office Action mailed Mar. 3, 2014", 14 pgs.
"U.S. Appl. No. 13/583,750, Preliminary Amendment filed Sep. 10, 2012", 3 pgs.
"U.S. Appl. No. 13/583,750, Response filed Feb. 12, 2014 to Restriction Requirement mailed Nov. 12, 2013", 8 pgs.
"U.S. Appl. No. 13/583,750, Response filed Jul. 1, 2014 to Non Final Office Action mailed Mar. 3, 2014", 13 pgs.
"U.S. Appl. No. 13/583,750, Response filed Oct. 30, 2014 to Final Office action mailed Jul. 30, 2014", 13 pgs.
"U.S. Appl. No. 13/583,750, Restriction Requirement mailed Nov. 12, 2013", 9 pgs.
"Chinese Application Serial. No. 201080021368.6, Office Action mailed Jul. 3, 2014", (w/Englinsh Translation), 25 pgs.
"Chinese Application Serial No. 201080021368.6, Response filed Sep. 18, 2014 to Office Action mailed Jul. 3, 2014", (w/English Translation of Amended Claims), 23 pgs.
"International Application Serial No. PCT/US11/27754, International Preliminary Report on Patentability dated Sep. 11, 2012", 6 pgs.
"International Application Serial No. PCT/US11/27754, International Search Report mailed May 18, 2011", 3 pgs.
"International Application Serial No. PCT/US11/27754, Written Opinion mailed May 18, 2011", 5 pgs.
"International Application Serial No. PCT/US2010/027361, International Search Report mailed Nov. 4, 2010", 6 pgs.
Afaneh, C., et al., "Urinary Cell Levels of mRNA for OX40, OX40L, PD-1, PD-L1 or PD-L2 and Acute Rejection of Human Renal Allografts", Transplantation, 90(12), (2010), 14 pgs.
Anglicheau, Dany, et al., "Noninvasive Prediction of Organ Graft Rejection and Outcome Using Gene Expression Patterns", Transplantation, 86(2), (2008), 15 pgs.
Aquino-Dias, E. C., et al., "Non-invasive diagnosis of acute rejection in kidney transplants with delayed graft function", Kidney International 73(7), (2008), 877-884.
Chang, Alexander T., et al., "The role of antibodies in transplantation", Transplantation Reviews, 23(4), (2009), 191-198.
Chen, G., et al., "Discordant Protein and mRNA Expression in Lung Adenocarcinomas", Molecular & Cellular Proteomics 1(4), (2002), 304-313.
Cheung, V. G., et al., "Natural variation in human gene expression assessed in lymphoblastoid cells", Nature Genetics, 33(3), (Mar. 2003), 422-425.
Cobb, J P, et al., "Sepsis gene expression profiling: Murine splenic compared with hepatic responses determined by using complementary DNA microarrays", Crit Care Med, 30(12), (2002), 2711-2721.
Dadhania, D., et al., "Molecular signatures of urinary cells distinguish acute rejection of renal allografts from urinary tract infection", (Abstract Only), Transplantation, 75 (10), 1752-1754, (2003), 1 pg.
Ding, R., et al,, "CD102 mRNA Levels in Urinary Cells Predict Acute Rejection of Renal Allografts", Transplantation, 75(8), (2003), 1307-1312.
Ding, R., et al., "Noninvasive Diagnosis of BK Virus Nephritis by Measurement of Messenger RNA for BK Virus VP1 in Urine", Transplantation, 74(7), (2002), 987-994.
Flechner, S. M., et al., "Kidney Transplant Rejection and Tissue of Biopsies and Peripheral Blood Lymphocytes", American Journal of Transplantation, 4(9), (2004), 1475-1489.
Gibson, U. E., et al., "A Novel Method for Real Time Quantitative RT-PCR", Genome Research, 6(10), (1996), 995-1001.
Heid, C. A., et al., "Real Time Quantitative PCR", Genome Research, 6(10), (1996), 986-994.
Hoshikawa, Y., et al., "Hypoxia induces different genes in the lungs of rats compared with mice", Physiol Genomics 12(3), (2003), 209-219.
Hsieh, M.-F., et al., "Both CXCR3 and CXCL10/1FN-Inducible Protein 10 are Required for Resistance to Primary Infection by Dengue Virus", J Immunol. 177, (2006), 1855-1863.
Kalaaji, M., et al., "Glomerular apoptotic nucleosomes are central target structures for nephritogenic antibodies in human SLE nephritis", Kidney International, 71(7), (2007), 664-672.
Kotsch, K., et al., "Enhanced granulysin mrna expression in urinary sediment in early and delayed acute renal allograft rejection", Transplantation, 77(12), (2004), 1866-1875.
Muthukumar, T., et al., "Messenger RNA for FOXP3 in the Urine of Renal-Allograft Receipients", New England Journal of Medicine, 353(22), (2005), 2342-2351.
Muthukumar, T., et al., "Serine Proteinase Inhibitor-9, an Endogenous Blocker of Granzyme B/Perforin Lytic Pathway, is Hyperexpressed During Acute Rejection of Renal Allografts", Transplantation, 75(9), (2003), 1565-1570.
Prashar, Y., et al., "Analysis of differential gene expression by display of 3' end restriction fragments of cDNA's", Proc. Natl. Acad. Sci. USA, 93(2), (Jan. 1996), 659-663.
Tatapudi, R. R., et al., "Noninvasive detection of renal allograft inflammation by measurements of mRNA for IP-10 and CXCR3 in urine", Kidney International, 65(6), (2004), 2390-2397.
Tyagi, S. et al., "Beacons of Light", Nature Biotechnology, 24(3), (1996), 303-304.
Velculescu, V. E., et al., "Serial Analysis of Gene Expression", Science, 270(5235), (1995), 484-487.
Zhang, Z., et al., "A Linear Regression Framework for Receiver Operating Characteristics (ROC) Curve Analysis", University of Washington Biostatistics Working Paper Series, 2005), 23 pgs.
"U.S. Appl. No. 13/583,750, Examiner Interview Summary mailed Oct. 10, 2014", 3 pgs.
"U.S. Appl. No. 13/583,750, Examiner Interview Summary mailed Nov. 12, 2015", 3 pgs.
"U.S. Appl. No. 13/583,750, Response filed Nov. 9, 2015 to Non Final Office Action mailed Jul. 9, 2015", 16 pgs.
"European Application Serial No. 10751549.6, Extended European Search Report mailed Aug. 13, 2015", 9 pgs.
"U.S. Appl. No. 13/583,750, Non Final Office Action mailed Jul. 9, 2015", 18 pgs.
"Chinese Application Serial No. 201080021368.6, Decision mailed Aug. 6, 2015", (w/ English Summary), 8 pgs.
"Chinese Application Serial No. 201080021368.6, Office Action mailed Jan. 20, 2015", (w/ English Translation), 15 pgs.
"Chinese Application Serial No. 201080021368.6, Response filed Apr. 3, 2015 to Office Action mailed Jan. 20, 2015", (w/ English Translation of Claims), 19 pgs.
"European Application Serial No. 10751549.6, Office Action mailed Apr. 11, 2014", 3 pgs.
Veronese, F., et al., "Pathological and Clinical Correlates of FOXP3+ Cells in Renal Allografts during Acute Rejection", American Journal of Transplantation; 7(4), (2007), 914-922.
"U.S. Appl. No. 13/583,750, Response filed May 18, 2016 to Final Office Action mailed Jan. 25, 2016", 17 pgs.

(56) References Cited

OTHER PUBLICATIONS

"U.S. Appl. No. 13/583,750, Advisory Action mailed May 11, 2016", 4 pgs.
"U.S. Appl. No. 13/583,750, Response filed Apr. 22, 2016 to Final Office Action mailed Jan. 25, 2016", 16 pgs.
"U.S. Appl. No. 13/583,750, Non Final Office Action mailed Dec. 1, 2016", 20 pgs.
"U.S. Appl. No. 13/583,750, Notice of Allowance dated May 18, 2017", 9 pgs.
"Chinese Application Serial No. 201080021368.6, Reexamination Decision dated Jun. 5, 2017", (w/ English Translation), 34 pgs.
"European Application Serial No. 10751549.6, Response Filed Aug. 21, 2017 to Communication Pursuant to Article 94(3). EPC dated Apr. 18, 2017", 10 pgs.
"U.S. Appl. No. 13/583,750, Response filed Apr. 3, 2017 to Non Final Office Action dated Dec. 1, 2016", 15 pgs.
"Chinese Application Serial No. 201080021368.6, Office Action dated Dec. 21, 2016", With English Translation, 15 pgs.
"Chinese Application Serial No. 201080021368.6, Response filed Feb. 3, 2017 to Office Action dated Dec. 21, 2016", With English Translation of Claims, 11 pgs.
"European Application Serial No. 10751549.6, Communication Pursuant to Article 94(3) EPC dated Apr. 18, 2017", 6 pgs.
Hamdorf, Matthias, et al., "The Potential of MicroRNAs as Novel Biomarkers for Transplant Rejection", Journal of Immunology Research, vol. 2017, Article ID 4072364, [Online]. Retrieved from the Internet: <URL: https://doi.org/10.1155/2017/4072364>, 12 pgs.

* cited by examiner

Figure 9
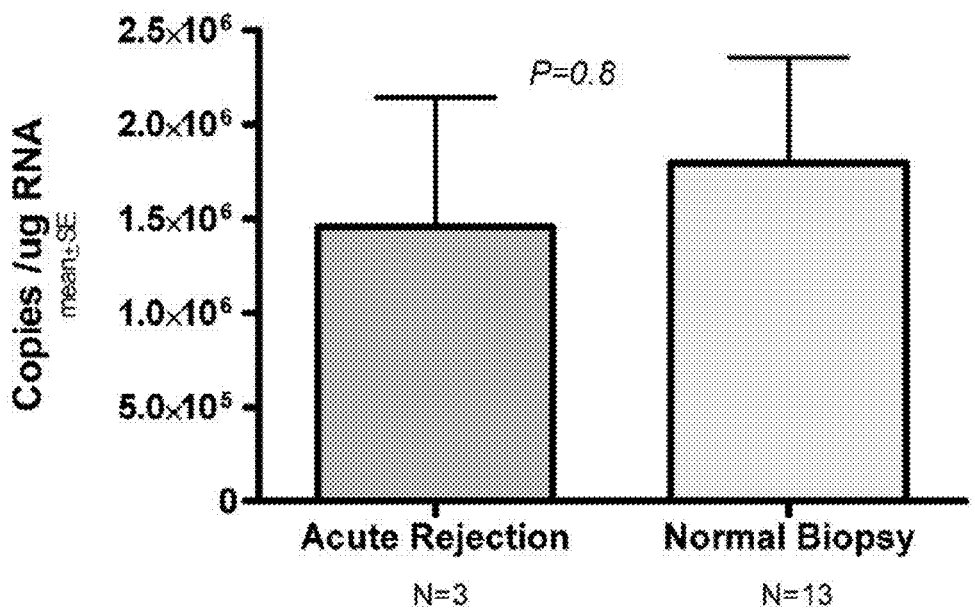
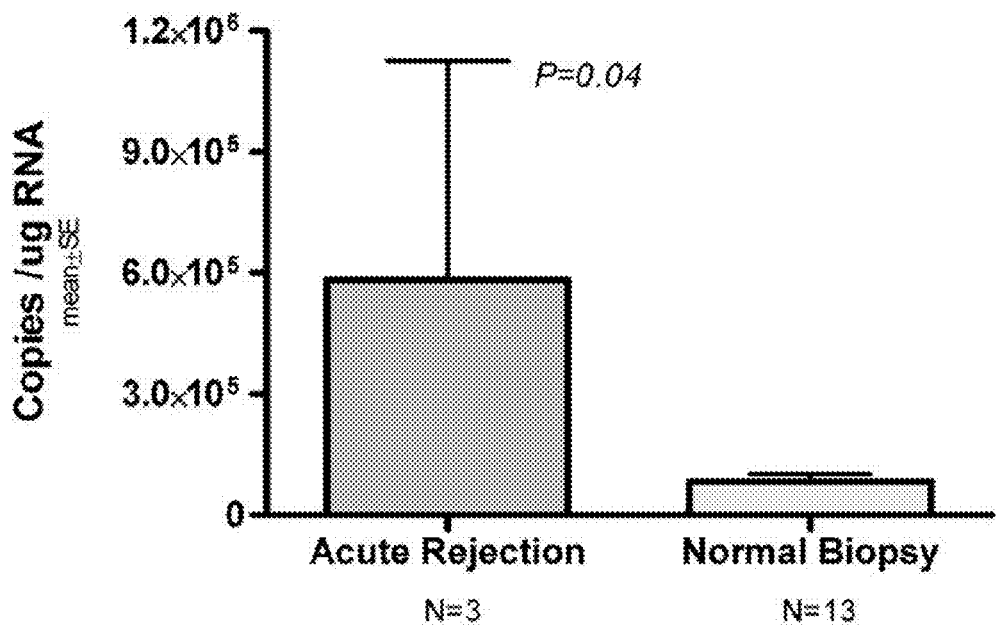

```
                        SEQUENCE LISTING

<160> NUMBER OF SEQ ID NOS: 86

<210> SEQ ID NO 1
<211> LENGTH: 20
<212> TYPE: RNA
<213> ORGANISM: Artificial Sequence
<220> FEATURE:
<223> OTHER INFORMATION: Synthetic nucleotide sequence: miR-142-5p

<400> SEQUENCE: 1
cauaaaguag aaagcacuac                                                   20

<210> SEQ ID NO 2
<211> LENGTH: 23
<212> TYPE: RNA
<213> ORGANISM: Artificial Sequence
<220> FEATURE:
<223> OTHER INFORMATION: Synthetic nucleotide sequence: miR-142-3p

<400> SEQUENCE: 2
uguaguguuu ccuacuuuau gga                                               23

<210> SEQ ID NO 3
<211> LENGTH: 22
<212> TYPE: RNA
<213> ORGANISM: Artificial Sequence
<220> FEATURE:
<223> OTHER INFORMATION: Synthetic nucleotide sequence: miR-155

<400> SEQUENCE: 3
uuaaugcuaa ucgugauagg gg                                                22

<210> SEQ ID NO 4
<211> LENGTH: 22
<212> TYPE: RNA
<213> ORGANISM: Artificial Sequence
<220> FEATURE:
<223> OTHER INFORMATION: Synthetic nucleotide sequence: miR-146a

<400> SEQUENCE: 4
ugagaacuga auuccauggg uu                                                22

<210> SEQ ID NO 5
<211> LENGTH: 22
<212> TYPE: RNA
<213> ORGANISM: Artificial Sequence
<220> FEATURE:
<223> OTHER INFORMATION: Synthetic nucleotide sequence: miR-146b

<400> SEQUENCE: 5
ugagaacuga auuccauagg cu                                                22

<210> SEQ ID NO 6
<211> LENGTH: 24
<212> TYPE: RNA
<213> ORGANISM: Artificial Sequence
<220> FEATURE:
<223> OTHER INFORMATION: Synthetic nucleotide sequence: miR-342

<400> SEQUENCE: 6
ucucacacag aaaucgcacc cguc                                              24
```

```
<210> SEQ ID NO 7
<211> LENGTH: 21
<212> TYPE: RNA
<213> ORGANISM: Artificial Sequence
<220> FEATURE:
<223> OTHER INFORMATION: Synthetic nucleotide sequence: miR-650

<400> SEQUENCE: 7
aggaggcagc gcucucagga c                                              21

<210> SEQ ID NO 8
<211> LENGTH: 22
<212> TYPE: RNA
<213> ORGANISM: Artificial Sequence
<220> FEATURE:
<223> OTHER INFORMATION: Synthetic nucleotide sequence: miR-21

<400> SEQUENCE: 8
uagcuuauca gacugauguu ga                                             22

<210> SEQ ID NO 9
<211> LENGTH: 23
<212> TYPE: RNA
<213> ORGANISM: Artificial Sequence
<220> FEATURE:
<223> OTHER INFORMATION: Synthetic nucleotide sequence: miR-425-5p

<400> SEQUENCE: 9
aaugacacga ucacucccgu uga                                            23

<210> SEQ ID NO 10
<211> LENGTH: 23
<212> TYPE: RNA
<213> ORGANISM: Artificial Sequence
<220> FEATURE:
<223> OTHER INFORMATION: Synthetic nucleotide sequence: miR-30c

<400> SEQUENCE: 10
uguaaacauc cuacacucuc agc                                            23

<210> SEQ ID NO 11
<211> LENGTH: 22
<212> TYPE: RNA
<213> ORGANISM: Artificial Sequence
<220> FEATURE:
<223> OTHER INFORMATION: Synthetic nucleotide sequence: miR-30a-3p

<400> SEQUENCE: 11
cuuucagucg gauguuugca gc                                             22

<210> SEQ ID NO 12
<211> LENGTH: 23
<212> TYPE: RNA
<213> ORGANISM: Artificial Sequence
<220> FEATURE:
<223> OTHER INFORMATION: Synthetic nucleotide sequence: miR-10a

<400> SEQUENCE: 12
uacccuguag auccgaauuu gug                                            23

<210> SEQ ID NO 13
<211> LENGTH: 22
<212> TYPE: RNA
<213> ORGANISM: Artificial Sequence
<220> FEATURE:
<223> OTHER INFORMATION: Synthetic nucleotide sequence: miR-30e-3p
```

```
<400> SEQUENCE: 13
cuuucagucg gauguuuaca gc                                              22

<210> SEQ ID NO 14
<211> LENGTH: 22
<212> TYPE: RNA
<213> ORGANISM: Artificial Sequence
<220> FEATURE:
<223> OTHER INFORMATION: Synthetic nucleotide sequence: miR-30b

<400> SEQUENCE: 14
uguaaacauc cuacacucag cu                                              22

<210> SEQ ID NO 15
<211> LENGTH: 22
<212> TYPE: RNA
<213> ORGANISM: Artificial Sequence
<220> FEATURE:
<223> OTHER INFORMATION: Synthetic nucleotide sequence: miR-10b

<400> SEQUENCE: 15
uacccuguag aaccgaauuu gu                                              22

<210> SEQ ID NO 16
<211> LENGTH: 21
<212> TYPE: RNA
<213> ORGANISM: Artificial Sequence
<220> FEATURE:
<223> OTHER INFORMATION: Synthetic nucleotide sequence: miR-32

<400> SEQUENCE: 16
uauugcacau uacuaaguug c                                               21

<210> SEQ ID NO 17
<211> LENGTH: 23
<212> TYPE: RNA
<213> ORGANISM: Artificial Sequence
<220> FEATURE:
<223> OTHER INFORMATION: Synthetic nucleotide sequence: miR-9

<400> SEQUENCE: 17
ucuuugguua ucuagcugua uga                                             23

<210> SEQ ID NO 18
<211> LENGTH: 24
<212> TYPE: RNA
<213> ORGANISM: Artificial Sequence
<220> FEATURE:
<223> OTHER INFORMATION: Synthetic nucleotide sequence: miR-193b

<400> SEQUENCE: 18
aacuggcccu caaagucccg cuuu                                            24

<210> SEQ ID NO 19
<211> LENGTH: 22
<212> TYPE: RNA
<213> ORGANISM: Artificial Sequence
<220> FEATURE:
<223> OTHER INFORMATION: Synthetic nucleotide sequence: miR-143

<400> SEQUENCE: 19
ugagaugaag cacuguagcu ca                                              22

<210> SEQ ID NO 20
```

```
<211> LENGTH: 23
<212> TYPE: RNA
<213> ORGANISM: Artificial Sequence
<220> FEATURE:
<223> OTHER INFORMATION: Synthetic nucleotide sequence: miR-489

<400> SEQUENCE: 20
agugacauca cauauacggc agc                                        23

<210> SEQ ID NO 21
<211> LENGTH: 21
<212> TYPE: RNA
<213> ORGANISM: Artificial Sequence
<220> FEATURE:
<223> OTHER INFORMATION: Synthetic nucleotide sequence: miR-27b

<400> SEQUENCE: 21
uucacagugg cuaaguucug c                                          21

<210> SEQ ID NO 22
<211> LENGTH: 21
<212> TYPE: RNA
<213> ORGANISM: Artificial Sequence
<220> FEATURE:
<223> OTHER INFORMATION: Synthetic nucleotide sequence: miR-126

<400> SEQUENCE: 22
cauuauuacu uuggguacgc g                                          21

<210> SEQ ID NO 23
<211> LENGTH: 21
<212> TYPE: RNA
<213> ORGANISM: Artificial Sequence
<220> FEATURE:
<223> OTHER INFORMATION: Synthetic nucleotide sequence: miR-193a

<400> SEQUENCE: 23
aacuggccua caaaguccca g                                          21

<210> SEQ ID NO 24
<211> LENGTH: 22
<212> TYPE: RNA
<213> ORGANISM: Artificial Sequence
<220> FEATURE:
<223> OTHER INFORMATION: Synthetic nucleotide sequence: miR-378

<400> SEQUENCE: 24
cuccugacuc cagguccugu gu                                         22

<210> SEQ ID NO 25
<211> LENGTH: 22
<212> TYPE: RNA
<213> ORGANISM: Artificial Sequence
<220> FEATURE:
<223> OTHER INFORMATION: Synthetic nucleotide sequence: miR-429

<400> SEQUENCE: 25
uaauacuguc ugguaaaacc gu                                         22

<210> SEQ ID NO 26
<211> LENGTH: 22
<212> TYPE: RNA
<213> ORGANISM: Artificial Sequence
<220> FEATURE:
<223> OTHER INFORMATION: Synthetic nucleotide sequence: miR-181c

<400> SEQUENCE: 26
```

```
aacauucaac cugucgguga gu                                          22

<210> SEQ ID NO 27
<211> LENGTH: 21
<212> TYPE: RNA
<213> ORGANISM: Artificial Sequence
<220> FEATURE:
<223> OTHER INFORMATION: Synthetic nucleotide sequence: miR-196b

<400> SEQUENCE: 27
uagguaguuu ccuguuguug g                                           21

<210> SEQ ID NO 28
<211> LENGTH: 23
<212> TYPE: RNA
<213> ORGANISM: Artificial Sequence
<220> FEATURE:
<223> OTHER INFORMATION: Synthetic nucleotide sequence: miR-199a

<400> SEQUENCE: 28
cccaguguuc agacuaccug uuc                                         23

<210> SEQ ID NO 29
<211> LENGTH: 22
<212> TYPE: RNA
<213> ORGANISM: Artificial Sequence
<220> FEATURE:
<223> OTHER INFORMATION: Synthetic nucleotide sequence: miR-660

<400> SEQUENCE: 29
uacccauugc auaucggagu ug                                          22

<210> SEQ ID NO 30
<211> LENGTH: 22
<212> TYPE: RNA
<213> ORGANISM: Artificial Sequence
<220> FEATURE:
<223> OTHER INFORMATION: Synthetic nucleotide sequence: miR-203

<400> SEQUENCE: 30
gugaaauguu uaggaccacu ag                                          22

<210> SEQ ID NO 31
<211> LENGTH: 22
<212> TYPE: RNA
<213> ORGANISM: Artificial Sequence
<220> FEATURE:
<223> OTHER INFORMATION: Synthetic nucleotide sequence: miR-204

<400> SEQUENCE: 31
uucccuuugu cauccuaugc cu                                          22

<210> SEQ ID NO 32
<211> LENGTH: 20
<212> TYPE: RNA
<213> ORGANISM: Artificial Sequence
<220> FEATURE:
<223> OTHER INFORMATION: Synthetic nucleotide sequence: miR-30e-5p

<400> SEQUENCE: 32
uguaaacauc cuugacugga                                             20

<210> SEQ ID NO 33
<211> LENGTH: 22
<212> TYPE: RNA
```

<213> ORGANISM: Artificial Sequence
<220> FEATURE:
<223> OTHER INFORMATION: Synthetic nucleotide sequence: miR-30a-5p

<400> SEQUENCE: 33
uguaaacauc cucgacugga ag                                          22

<210> SEQ ID NO 34
<211> LENGTH: 22
<212> TYPE: RNA
<213> ORGANISM: Artificial Sequence
<220> FEATURE:
<223> OTHER INFORMATION: Synthetic nucleotide sequence: miR-30d

<400> SEQUENCE: 34
uguaaacauc cccgacugga ag                                          22

<210> SEQ ID NO 35
<211> LENGTH: 22
<212> TYPE: RNA
<213> ORGANISM: Artificial Sequence
<220> FEATURE:
<223> OTHER INFORMATION: Synthetic nucleotide sequence: miR-125b

<400> SEQUENCE: 35
ucccugagac ccuaacuugu ga                                          22

<210> SEQ ID NO 36
<211> LENGTH: 22
<212> TYPE: RNA
<213> ORGANISM: Artificial Sequence
<220> FEATURE:
<223> OTHER INFORMATION: Synthetic nucleotide sequence: miR-130a

<400> SEQUENCE: 36
cagugcaaug uuaaaagggc au                                          22

<210> SEQ ID NO 37
<211> LENGTH: 21
<212> TYPE: RNA
<213> ORGANISM: Artificial Sequence
<220> FEATURE:
<223> OTHER INFORMATION: Synthetic nucleotide sequence: miR-126

<400> SEQUENCE: 37
ucguaccgug aguaauaaug c                                           21

<210> SEQ ID NO 38
<211> LENGTH: 21
<212> TYPE: RNA
<213> ORGANISM: Artificial Sequence
<220> FEATURE:
<223> OTHER INFORMATION: Synthetic nucleotide sequence: miR-195

<400> SEQUENCE: 38
uagcagcaca gaaauauugg c                                           21

<210> SEQ ID NO 39
<211> LENGTH: 21
<212> TYPE: RNA
<213> ORGANISM: Artificial Sequence
<220> FEATURE:
<223> OTHER INFORMATION: Synthetic nucleotide sequence: miR-26a

<400> SEQUENCE: 39
uucaaguaau ccaggauagg c                                           21

```
<210> SEQ ID NO 40
<211> LENGTH: 22
<212> TYPE: RNA
<213> ORGANISM: Artificial Sequence
<220> FEATURE:
<223> OTHER INFORMATION: Synthetic nucleotide sequence: miR-26b

<400> SEQUENCE: 40
uucaaguaau ucaggauagg uu                                              22

<210> SEQ ID NO 41
<211> LENGTH: 21
<212> TYPE: RNA
<213> ORGANISM: Artificial Sequence
<220> FEATURE:
<223> OTHER INFORMATION: Synthetic nucleotide sequence: miR-497

<400> SEQUENCE: 41
cagcagcaca cugugguuug u                                               21

<210> SEQ ID NO 42
<211> LENGTH: 22
<212> TYPE: RNA
<213> ORGANISM: Artificial Sequence
<220> FEATURE:
<223> OTHER INFORMATION: Synthetic nucleotide sequence: miR-152

<400> SEQUENCE: 42
ucagugcaug acagaacuug gg                                              22

<210> SEQ ID NO 43
<211> LENGTH: 22
<212> TYPE: RNA
<213> ORGANISM: Artificial Sequence
<220> FEATURE:
<223> OTHER INFORMATION: Synthetic nucleotide sequence: miR-141

<400> SEQUENCE: 43
uaacacuguc ugguaaagau gg                                              22

<210> SEQ ID NO 44
<211> LENGTH: 21
<212> TYPE: RNA
<213> ORGANISM: Artificial Sequence
<220> FEATURE:
<223> OTHER INFORMATION: Synthetic nucleotide sequence: miR-296

<400> SEQUENCE: 44
agggcccccc cucaauccug u                                               21

<210> SEQ ID NO 45
<211> LENGTH: 22
<212> TYPE: RNA
<213> ORGANISM: Artificial Sequence
<220> FEATURE:
<223> OTHER INFORMATION: Synthetic nucleotide sequence: miR-365

<400> SEQUENCE: 45
uaaugccccu aaaauccuu au                                               22

<210> SEQ ID NO 46
<211> LENGTH: 22
<212> TYPE: RNA
<213> ORGANISM: Artificial Sequence
<220> FEATURE:
```

<223> OTHER INFORMATION: Synthetic nucleotide sequence: miR-99a

<400> SEQUENCE: 46
aacccguaga uccgaucuug ug                                          22

<210> SEQ ID NO 47
<211> LENGTH: 22
<212> TYPE: RNA
<213> ORGANISM: Artificial Sequence
<220> FEATURE:
<223> OTHER INFORMATION: Synthetic nucleotide sequence: miR-100

<400> SEQUENCE: 47
aacccguaga uccgaacuug ug                                          22

<210> SEQ ID NO 48
<211> LENGTH: 23
<212> TYPE: RNA
<213> ORGANISM: Artificial Sequence
<220> FEATURE:
<223> OTHER INFORMATION: Synthetic nucleotide sequence: miR-186

<400> SEQUENCE: 48
caaagaauuc uccuuuuggg cuu                                         23

<210> SEQ ID NO 49
<211> LENGTH: 22
<212> TYPE: RNA
<213> ORGANISM: Artificial Sequence
<220> FEATURE:
<223> OTHER INFORMATION: Synthetic nucleotide sequence: let-7a

<400> SEQUENCE: 49
ugagguagua gguuguauag uu                                          22

<210> SEQ ID NO 50
<211> LENGTH: 21
<212> TYPE: RNA
<213> ORGANISM: Artificial Sequence
<220> FEATURE:
<223> OTHER INFORMATION: Synthetic nucleotide sequence: miR-223

<400> SEQUENCE: 50
ugucaguuug ucaaauaccc c                                           21

<210> SEQ ID NO 51
<211> LENGTH: 22
<212> TYPE: RNA
<213> ORGANISM: Artificial Sequence
<220> FEATURE:
<223> OTHER INFORMATION: Synthetic nucleotide sequence: let-7c

<400> SEQUENCE: 51
ugagguagua gguuguaugg uu                                          22

<210> SEQ ID NO 52
<211> LENGTH: 23
<212> TYPE: RNA
<213> ORGANISM: Artificial Sequence
<220> FEATURE:
<223> OTHER INFORMATION: Synthetic nucleotide sequence: miR-125a

<400> SEQUENCE: 52
ucccugagac ccuuuaaccu gug                                         23

```
<210> SEQ ID NO 53
<211> LENGTH: 22
<212> TYPE: RNA
<213> ORGANISM: Artificial Sequence
<220> FEATURE:
<223> OTHER INFORMATION: Synthetic nucleotide sequence: miR-200a

<400> SEQUENCE: 53
uaacacuguc ugguaacgau gu                                              22

<210> SEQ ID NO 54
<211> LENGTH: 26
<212> TYPE: DNA
<213> ORGANISM: Artificial Sequence
<220> FEATURE:
<223> OTHER INFORMATION: Synthetic nucleotide sequence

<400> SEQUENCE: 54
aagaaatggg tggtattaca cagaca                                          26

<210> SEQ ID NO 55
<211> LENGTH: 27
<212> TYPE: DNA
<213> ORGANISM: Artificial Sequence
<220> FEATURE:
<223> OTHER INFORMATION: Synthetic nucleotide sequence

<400> SEQUENCE: 55
aagaaatggg tggtattaca cagacat                                         27

<210> SEQ ID NO 56
<211> LENGTH: 33
<212> TYPE: DNA
<213> ORGANISM: Artificial Sequence
<220> FEATURE:
<223> OTHER INFORMATION: Synthetic nucleotide sequence

<400> SEQUENCE: 56
ccatctctgg aaccacagta atattgacat gcc                                  33

<210> SEQ ID NO 57
<211> LENGTH: 25
<212> TYPE: DNA
<213> ORGANISM: Artificial Sequence
<220> FEATURE:
<223> OTHER INFORMATION: Synthetic nucleotide sequence

<400> SEQUENCE: 57
aactccccat ctacccaata ctgtt                                           25

<210> SEQ ID NO 58
<211> LENGTH: 23
<212> TYPE: DNA
<213> ORGANISM: Artificial Sequence
<220> FEATURE:
<223> OTHER INFORMATION: Synthetic nucleotide sequence

<400> SEQUENCE: 58
agaaggcaaa gatcagcatc act                                             23

<210> SEQ ID NO 59
<211> LENGTH: 31
<212> TYPE: DNA
<213> ORGANISM: Artificial Sequence
<220> FEATURE:
<223> OTHER INFORMATION: Synthetic nucleotide sequence
```

<400> SEQUENCE: 59
cagcatacaa tctctgttct tgggcatttt g                                       31

<210> SEQ ID NO 60
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 60
tcacgagcaa ctcgcaaaga                                                    20

<210> SEQ ID NO 61
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 61
tcccatcacc gttagcaact c                                                  21

<210> SEQ ID NO 62
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 62
tgtggcagtc accccaagtt cagc                                               24

<210> SEQ ID NO 63
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 63
tggaggcagg catttcagta a                                                  21

<210> SEQ ID NO 64
<211> LENGTH: 17
<212> TYPE: DNA
<213> ORGANISM: Artificial Sequence
<220> FEATURE:
<223> OTHER INFORMATION: Synthetic nucleotide sequence

<400> SEQUENCE: 64
ttcccggcaa cccactt                                                       17

<210> SEQ ID NO 65
<211> LENGTH: 25
<212> TYPE: DNA
<213> ORGANISM: Artificial Sequence
<220> FEATURE:
<223> OTHER INFORMATION: Synthetic nucleotide sequence

<400> SEQUENCE: 65
cccgagtgtt ccgatccagt ccagt                                              25

<210> SEQ ID NO 66
<211> LENGTH: 21

```
<212> TYPE: DNA
<213> ORGANISM: Artificial Sequence
<220> FEATURE:
<223> OTHER INFORMATION: Synthetic nucleotide sequence

<400> SEQUENCE: 66
tgtgtgtgtt tgccatcaac a                                              21

<210> SEQ ID NO 67
<211> LENGTH: 23
<212> TYPE: DNA
<213> ORGANISM: Artificial Sequence
<220> FEATURE:
<223> OTHER INFORMATION: Synthetic nucleotide sequence

<400> SEQUENCE: 67
cgtttgatct gctccctgta ctg                                            23

<210> SEQ ID NO 68
<211> LENGTH: 19
<212> TYPE: DNA
<213> ORGANISM: Artificial Sequence
<220> FEATURE:
<223> OTHER INFORMATION: Synthetic nucleotide sequence

<400> SEQUENCE: 68
caccaagtct tttgaggac                                                 19

<210> SEQ ID NO 69
<211> LENGTH: 17
<212> TYPE: DNA
<213> ORGANISM: Artificial Sequence
<220> FEATURE:
<223> OTHER INFORMATION: Synthetic nucleotide sequence

<400> SEQUENCE: 69
acaccgccca ccaccag                                                   17

<210> SEQ ID NO 70
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 70
tccacagaaa caacatcgat ttct                                           24

<210> SEQ ID NO 71
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 71
aggaacaaga agatgagg                                                  18

<210> SEQ ID NO 72
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 72
```
catagcagcc accttcattc c            21

<210> SEQ ID NO 73
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 73
tctgcactga gatcttccta ttgg         24

<210> SEQ ID NO 74
<211> LENGTH: 26
<212> TYPE: DNA
<213> ORGANISM: Artificial Sequence
<220> FEATURE:
<223> OTHER INFORMATION: Synthetic nucleotide sequence

<400> SEQUENCE: 74
cagatgcaat caatgcccca gtcacc       26

<210> SEQ ID NO 75
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 75
tctgcgctcc tgcatctg               18

<210> SEQ ID NO 76
<211> LENGTH: 18
<212> TYPE: DNA
<213> ORGANISM: Artificial Sequence
<220> FEATURE:
<223> OTHER INFORMATION: Synthetic nucleotide sequence

<400> SEQUENCE: 76
agtgggcggg caatgtag               18

<210> SEQ ID NO 77
<211> LENGTH: 22
<212> TYPE: DNA
<213> ORGANISM: Artificial Sequence
<220> FEATURE:
<223> OTHER INFORMATION: Synthetic nucleotide sequence

<400> SEQUENCE: 77
tcggacacca caccctgctg ct          22

<210> SEQ ID NO 78
<211> LENGTH: 22
<212> TYPE: DNA
<213> ORGANISM: Artificial Sequence
<220> FEATURE:
<223> OTHER INFORMATION: Synthetic nucleotide sequence

<400> SEQUENCE: 78
tgtccacgtg ttgagatcat tg          22

<210> SEQ ID NO 79
<211> LENGTH: 20
<212> TYPE: DNA
<213> ORGANISM: Artificial Sequence

```
<220> FEATURE:
<223> OTHER INFORMATION: Synthetic nucleotide sequence

<400> SEQUENCE: 79
ggccttcgat tctggattca                                                     20

<210> SEQ ID NO 80
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 80
tacaatgaaa agaagggtg agaa                                                 24

<210> SEQ ID NO 81
<211> LENGTH: 20
<212> TYPE: DNA
<213> ORGANISM: Artificial Sequence
<220> FEATURE:
<223> OTHER INFORMATION: Synthetic nucleotide sequence

<400> SEQUENCE: 81
gcccgaagcg tttactttga                                                     20

<210> SEQ ID NO 82
<211> LENGTH: 24
<212> TYPE: DNA
<213> ORGANISM: Artificial Sequence
<220> FEATURE:
<223> OTHER INFORMATION: Synthetic nucleotide sequence

<400> SEQUENCE: 82
tccattattc ctagctgcgg tatc                                                24

<210> SEQ ID NO 83
<211> LENGTH: 19
<212> TYPE: DNA
<213> ORGANISM: Artificial Sequence
<220> FEATURE:
<223> OTHER INFORMATION: Synthetic nucleotide sequence

<400> SEQUENCE: 83
aaagcaggcc cgagccgcc                                                      19

<210> SEQ ID NO 84
<211> LENGTH: 21
<212> TYPE: DNA
<213> ORGANISM: Artificial Sequence
<220> FEATURE:
<223> OTHER INFORMATION: Synthetic nucleotide sequence

<400> SEQUENCE: 84
cccacatctg gagcagagtc a                                                   21

<210> SEQ ID NO 85
<211> LENGTH: 23
<212> TYPE: DNA
<213> ORGANISM: Artificial Sequence
<220> FEATURE:
<223> OTHER INFORMATION: Synthetic nucleotide sequence

<400> SEQUENCE: 85
cagatgccat ttttcaggtc ttg                                                 23
```

```
<210> SEQ ID NO 86
<211> LENGTH: 26
<212> TYPE: DNA
<213> ORGANISM: Artificial Sequence
<220> FEATURE:
<223> OTHER INFORMATION: Synthetic nucleotide sequence

<400> SEQUENCE: 86
caggtgacaa gtgacggtgg tctcca                                          26
```

METHOD TO ASSESS HUMAN ALLOGRAFT STATUS FROM MICRORNA EXPRESSION LEVELS

This application is a National Phase Application of International Application No. PCT/US2010/027361, filed on Mar. 15, 2010, which asserts priority to U.S. Provisional Application Ser. No. 61/160,188, filed on Mar. 13, 2009. Both aforementioned applications are hereby incorporated by reference in their entireties.

This invention was made with government support under grant numbers AI051652 and AI072790 awarded by the National Institutes of Health. The government has certain rights in the invention.

BACKGROUND OF THE INVENTION

Transplantation of organs has progressed from a risky experimental therapy to a safe and life-saving treatment modality in a relatively short span of five decades. However, transplant recipients require life-long treatment with non-specific, toxic, and multiple immunosuppressive drugs, and are ever under the threat of losing their allografts because of immune rejection of the transplanted organ.

Acute rejection of an organ transplanted from one human to another is an important risk factor for allograft failure. The outcome of acute rejection is, however, difficult to predict.

Currently, observation of histologic features in allograft tissue obtained by core needle biopsy is the best predictor whether an acute rejection will respond to anti-rejection therapy. However, the invasive procedure of allograft biopsy is associated with complications such as bleeding, arteriovenous fistula, and even graft loss. Thus, there is a need for a non-invasive method for determining whether a patient suffering from acute rejection of a transplant organ is at risk of loss of the transplanted organ.

SUMMARY OF THE INVENTION

The above need has been met by the present invention, which provides in one aspect, a method for assessing risk of organ rejection in a patient having a transplanted organ. The method includes measuring an amount of expression of a small non-coding marker RNA in a biological sample from the patient. The method further includes comparing the measured amount of expression of the small non-coding marker RNA in the patient to a reference amount of expression of the small non-coding marker RNA.

In one embodiment, the small non-coding marker RNA is selected from SEQ ID NOs: 1-9, or variants thereof, wherein an increase of expression of the small non-coding marker RNA that is equivalent to at least 1-fold as compared to the reference amount of expression of the small non-coding marker RNA indicates an increased risk of rejection of the transplanted organ.

In another embodiment, the small non-coding marker RNA is selected from SEQ ID NOs: 10-49, or variants thereof, wherein an increase of expression of the small non-coding marker RNA that is equivalent to less than 1-fold as compared to said reference amount of expression of the small non-coding marker RNA indicates an increased risk of rejection of said transplanted organ.

In a further embodiment, the method further includes (c) measuring a difference between the amount of expression of the small non-coding marker RNA in the biological sample and the reference amount of expression of said small non-coding marker RNA; (d) measuring an amount of expression of a endogenously expressed small non-coding reference RNA in a biological sample from the patient; (e) measuring a difference between the amount of expression of the endogenously expressed small non-coding reference RNA in the biological sample from the patient and a reference amount of expression of said endogenously expressed small non-coding reference RNA; (f) comparing the difference in step (c) to the difference in step (e); wherein a difference in step (c) that is greater than the difference in step (d) further indicates an increased risk of rejection of said transplanted organ.

In yet another embodiment, the method for assessing risk of organ rejection in a patient having a transplanted organ includes: (a) measuring an amount of expression of a small non-coding marker RNA in a biological sample from the patient, said small non-coding RNA selected from SEQ ID NOs: 1-9 or a combination thereof; (b) measuring an amount of expression of an endogenously expressed small non-coding reference RNA in a biological sample from the patient; (c) comparing the measured amount of step (a) to the measured amount of step (b) to determine a first ratio; (d) measuring an amount of expression of said small non-coding marker RNA in a biological sample from a person having a non-rejected organ, said small non-coding RNA selected from SEQ ID NOs: 1-9 or a combination thereof; (e) measuring an amount of expression of an endogenously expressed small non-coding reference RNA in a biological sample from the person having a non-rejected organ; and comparing the measured amount of step (d) to the measured amount of step (e) to determine a second ratio; wherein a calculation of the first ratio being greater than the second ratio by an amount equivalent to at least 1-fold indicates an increased risk of rejection of said transplanted organ.

In yet a further embodiment, the method for assessing risk of organ rejection in a patient having a transplanted organ includes: (a) measuring an amount of expression of a small non-coding marker RNA in a biological sample from the patient, said small non-coding RNA selected from SEQ ID NOs: 10-49, or a combination thereof; (b) measuring an amount of expression of an endogenously expressed small non-coding reference RNA in a biological sample from the patient; (c) comparing the measured amount of step (a) to the measured amount of step (b) to determine a first ratio; (d) measuring an amount of expression of said small non-coding marker RNA in a biological sample from a person having a non-rejected organ, said small non-coding RNA selected from the group consisting of SEQ ID NOs: 10-49, or a combination thereof; (e) measuring an amount of expression of an endogenously expressed small non-coding reference RNA in a biological sample from the person having a non-rejected organ; and comparing the measured amount of step (d) to the measured amount of step (e) to determine a second ratio; wherein a calculation of the first ratio being greater than the second ratio by at least an amount equivalent to less than 1-fold indicates an increased risk of rejection of said transplanted organ.

In yet an additional aspect, the invention relates to a kit for assessing risk of organ rejection in a patient having a transplanted organ. The kit includes at least one nucleic acid molecule complementary to a small non-coding marker RNA selected from the group consisting of SEQ ID NO: 1-49s, or variations thereof, and a means for measuring expression of a small non-coding marker RNA in a biological sample.

in acute rejection biopsies were quantified with the use of modified TaqMan miRNA assays. miRNA copy numbers were normalized using the RNU44 small nucleolar RNA copy numbers and are shown as mean (±SE) ratio of miRNA copies to RNU44 copy numbers. Results are from 2 consecutive experiments with 2 independent primary cultures of HRECs developed from 2 human kidneys. P values calculated using paired t test.

Figure 7:
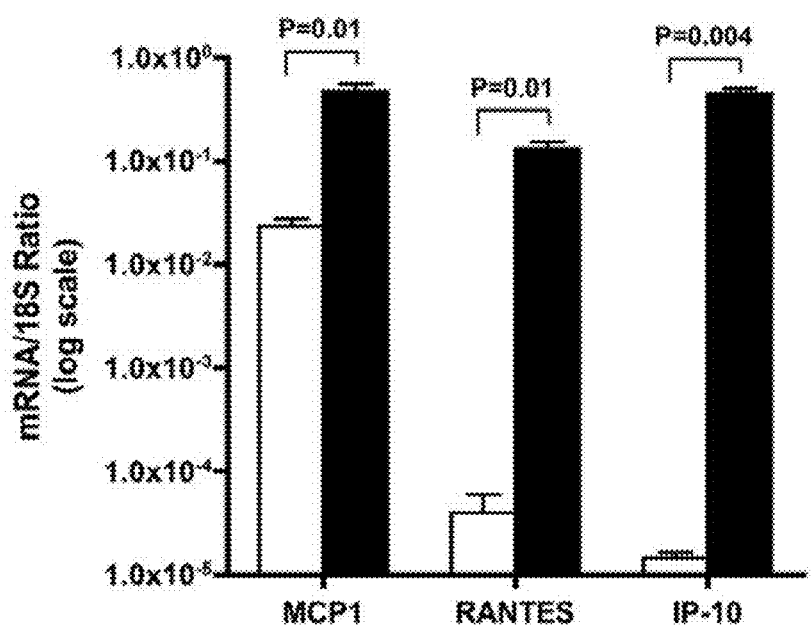

FIG. 7. Levels of chemokine mRNAs in resting or activated normal human renal epithelial cells. Primary cultures of normal human renal epithelial cells (HRECs) were incubated for 24 h with cell-free supernatants of resting PBMCs (open bars) or cell-free supernatants of PBMCs activated with 2 μg/mL PHA (filled bars). Total RNA was isolated from HRECs and the absolute levels of mRNA for the chemokines monocyte chemoattractant protein-1 (MCP1), regulated upon activation, normal T cell expressed and secreted (RANTES), and IFN-inducible protein-10 (IP-10) mRNAs were quantified with the use of real-time PCR assays. miRNA copy numbers were normalized using the 18S rRNA copy numbers, and are shown as mean (±SE) ratio of mRNA copies to 18S rRNA copies. Results are from 2 consecutive experiments with 2 independent primary cultures of HRECs developed from 2 human kidneys. P values calculated using paired t test.

Figure 8:
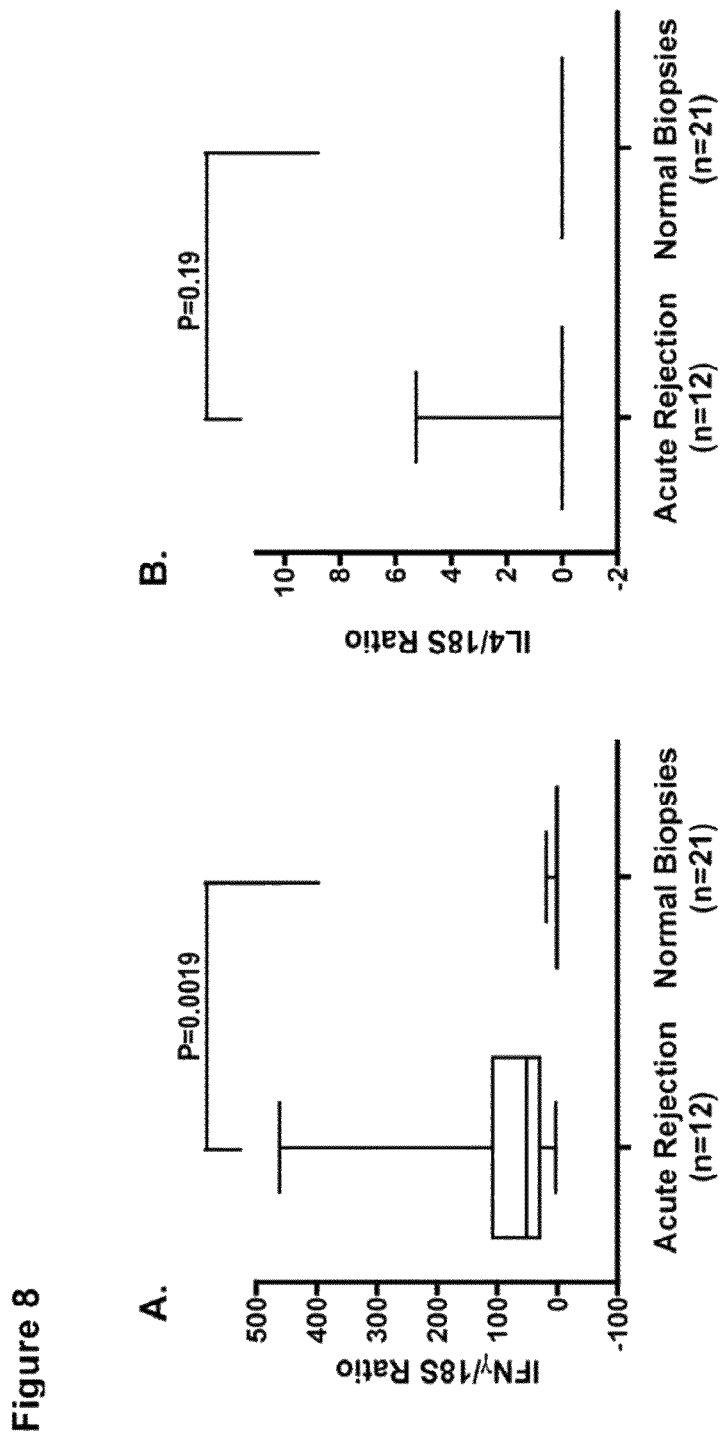

FIG. 8. Intragraft levels of mRNA in human renal allograft biopsies. Box and whisker plots show the 10th, 25th, 50th (median), 75th, and 90th percentile values for ratios of mRNA copies to 18S rRNA copies for IFN-γ (A) and interleukin-4 (B) in 12 acute rejection biopsies and 21 normal allograft biopsies of human renal allografts. The level of IFN-γ but not that of interleukin-4 was higher in acute rejection biopsies compared to normal allograft biopsies. Absolute levels of mRNAs were quantified using real-time quantitative PCR assays. P value calculated using t test.

FIG. 9. Urinary Cell Levels of miRNA 155 are diagnostic of acute rejection. Total RNA containing miRNAs was isolated from urinary cells collected from renal allograft recipients and levels of RNU44 (house keeping gene) and miRNA 155 were measured real time quantitative PCR assays. Urinary cell levels of miRNA 155 and not RNU 44 were significantly higher in urine from patients whose biopsies were classified acute rejection (n=3 specimens) compared to urine from patients with stable graft function and normal biopsy findings (n=13 specimens).

DETAILED DESCRIPTION OF THE INVENTION

The invention relates to methods and compositions for the non-invasive detection of organ rejection using a microRNA. The inventor discovered, among other things, that certain marker microRNAs (miRNA) are overexpressed or underexpressed in response to organ failure (e.g., acute rejection).

In one aspect, the invention relates to a method for assessing risk of organ rejection in a patient having a transplanted organ.

The patient having a transplanted organ is any human having a transplanted organ for which risk of organ rejection is to be assessed.

As used herein, the transplanted organ refers to any organ. Exemplary organs include kidney, heart, liver, lung, intestines, pancreas, pancreatic islets, etc.

Organ rejection refers to any failure of a transplanted organ resulting from an adverse immune response. For example, organ rejection includes acute and/or chronic rejection. An episode of acute rejection of an organ can be caused by an antibody-mediated or cell-mediated immune response. The cells involved in a cell-mediated immune response include, for example, activated cytotoxic T cells. An episode of acute rejection typcially occurs within fourteen days, more typically within ten days, and even more typically within five days after a transplant if the patient is not taking an immunosuppressant drug.

However, most if not all transplant patients are given immunosuppressant drugs. Thus, an episode of acute rejection generally occurs within about one year of a transplanted organ, more specifically within about nine months, even more specifically within about six months, and most specifically within about three months after transplant of an organ. Acute rejection, however, can occur at any time during the life of a transplanted organ. Further, a patient can have more than one episode of acute rejection of a transplanted organ.

Measuring an Amount of Expression of a Small Non-Coding Marker RNA

The method includes measuring an amount of expression of a small non-coding marker RNA in a biological sample from the patient.

As used herein, a small non-coding RNA refers to a ribonucleic acid sequence that does not code for a protein. For example, the small non-coding RNA may perform a regulatory function in the cell by regulating gene expression through sequence-specific base-pairing with complementary mRNA sequences.

A small non-coding RNA is less than about 40 nucleotides in length, preferably less than about 30 nucleotides, for example, about 29, 28, 27, 26, 25, 24, 23, 22, 21, or 20 nucleotides in length. The small non-coding RNA is more than about 10 nucleotides, for example, 11, 12, 13, 14, 15, 16, 17, 18, 19, or 20 nucleotides in length. Any maximum value can be combined with any minimum value to define a range.

Examples of a small non-coding RNA include transfer RNA (tRNA), ribosomal RNA (rRNA), microRNA (miRNA), small nuclear RNA (snRNA), small nucleolar RNA (snoRNA), and/or signal recognition particle RNA complex (SRP). Preferably, the small non-coding RNA is miRNA.

A small non-coding marker RNA as used herein refers to a small non-coding RNA that is used to assess risk of organ rejection. Specific examples of a small non-coding marker RNA include the following nucleic acid molecules and/or a nucleic acid molecule that has at least about 85%, 86%, 87%, 88%, 89%, 90%, 91%, 92%, 93%, 94%, 95%, 96%, 97%, 98%, or 99% sequence identity to a sequence set forth below:

```
                                        (SEQ ID NO: 1)
miR-142-5p  CAUAAAGUAGAAAGCACUAC (SEQ ID NO: 2)
miR-142-3p  UGUAGUGUUUCCUACUUUAUGGA (SEQ ID NO: 3)
miR-155     UUAAUGCUAAUCGUGAUAGGGG (SEQ ID NO: 4)
miR-146a    UGAGAACUGAAUUCCAUGGGUU (SEQ ID NO: 5)
miR-146b    UGAGAACUGAAUUCCAUAGGCU
```

-continued miR-342 UCUCACACAGAAAUCGCACCCGUC (SEQ ID NO: 6)

miR-650 AGGAGGCAGCGCUCUCAGGAC (SEQ ID NO: 7)

miR-21 UAGCUUAUCAGACUGAUGUUGA (SEQ ID NO: 8)

miR-425-5p AAUGACACGAUCACUCCCGUUGA (SEQ ID NO: 9)

miR-30c UGUAAACAUCCUACACUCUCAGC (SEQ ID NO: 10)

miR-30a-3p CUUUCAGUCGGAUGUUUGCAGC (SEQ ID NO: 11)

miR-10a UACCCUGUAGAUCCGAAUUUGUG (SEQ ID NO: 12)

miR-30e-3p CUUUCAGUCGGAUGUUUACAGC (SEQ ID NO: 13)

miR-30b UGUAAACAUCCUACACUCAGCU (SEQ ID NO: 14)

miR-10b UACCCUGUAGAACCGAAUUUGU (SEQ ID NO: 15)

miR-32 UAUUGCACAUUACUAAGUUGC (SEQ ID NO: 16)

miR-9 UCUUUGGUUAUCUAGCUGUAUGA (SEQ ID NO: 17)

miR-193b AACUGGCCCUCAAAGUCCCGCUUU (SEQ ID NO: 18)

miR-143 UGAGAUGAAGCACUGUAGCUCA (SEQ ID NO: 19)

miR-489 AGUGACAUCACAUAUACGGCAGC (SEQ ID NO: 20)

miR-27b UUCACAGUGGCUAAGUUCUGC (SEQ ID NO: 21)

miR-126 CAUUAUUACUUUUGGUACGCG (SEQ ID NO: 22)

miR-193a AACUGGCCUACAAAGUCCCAG (SEQ ID NO: 23)

miR-378 CUCCUGACUCCAGGUCCUGUGU (SEQ ID NO: 24)

miR-429 UAAUACUGUCUGGUAAAACCGU (SEQ ID NO: 25)

miR-181c AACAUUCAACCUGUCGGUGAGU (SEQ ID NO: 26)

miR-196b UAGGUAGUUUCCUGUUGUUGG (SEQ ID NO: 27)

miR-199a CCCAGUGUUCAGACUACCUGUUC (SEQ ID NO: 28)

miR-660 UACCCAUUGCAUAUCGGAGUUG (SEQ ID NO: 29)

miR-203 GUGAAAUGUUUAGGACCACUAG (SEQ ID NO: 30)

miR-204 UUCCCUUUGUCAUCCUAUGCCU (SEQ ID NO: 31)

miR-30e-5p UGUAAACAUCCUUGACUGGA (SEQ ID NO: 32)

-continued miR-30a-5p UGUAAACAUCCUCGACUGGAAG (SEQ ID NO: 33)

miR-30d UGUAAACAUCCCCGACUGGAAG (SEQ ID NO: 34)

miR-125b UCCCUGAGACCCUAACUUGUGA (SEQ ID NO: 35)

miR-130a CAGUGCAAUGUUAAAAGGGCAU (SEQ ID NO: 36)

miR-126 UCGUACCGUGAGUAAUAAUGC (SEQ ID NO: 37)

miR-195 UAGCAGCACAGAAAUAUUGGC (SEQ ID NO: 38)

miR-26a UUCAAGUAAUCCAGGAUAGGC (SEQ ID NO: 39)

miR-26b UUCAAGUAAUUCAGGAUAGGUU (SEQ ID NO: 40)

miR-497 CAGCAGCACACUGUGGUUUGU (SEQ ID NO: 41)

miR-152 UCAGUGCAUGACAGAACUUGGG (SEQ ID NO: 42)

miR-141 UAACACUGUCUGGUAAAGAUGG (SEQ ID NO: 43)

miR-296 AGGGCCCCCCCUCAAUCCUGU (SEQ ID NO: 44)

miR-365 UAAUGCCCCUAAAAAUCCUUAU (SEQ ID NO: 45)

miR-99a AACCCGUAGAUCCGAUCUUGUG (SEQ ID NO: 46)

miR-100 AACCCGUAGAUCCGAACUUGUG (SEQ ID NO: 47)

miR-186 CAAAGAAUUCUCCUUUUGGGCUU (SEQ ID NO: 48)

let-7a UGAGGUAGUAGGUUGUAUAGUU (SEQ ID NO: 49)

miR-223 UGUCAGUUUGUCAAAUACCCC (SEQ ID NO: 50)

let-7c UGAGGUAGUAGGUUGUAUGGUU (SEQ ID NO: 51)

miR-125a UCCCUGAGACCCUUUAACCUGUG (SEQ ID NO: 52)

miR-200a UAACACUGUCUGGUAACGAUGU (SEQ ID NO: 53)

Methods of determining sequence identity are known in the art. Percent nucleic acid sequence identity with respect to the small non-coding RNAs identified herein is defined as the percentage of nucleic acids in a candidate sequence that are identical with the nucleic acids in the specific small non-coding RNA sequence, after aligning the sequences and introducing gaps, if necessary, to achieve the maximum percent sequence identity, and not considering any conservative substitutions as part of the sequence identity.

Alignment for purposes of determining percent nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

For purposes herein, however, percent (%) nucleic acid sequence identity values are generated using the sequence comparison computer program NCBI-BLAST2 (Altschul et al., Nucleic Acids Res. 25:3389-3402 (1997)). The NCBI-BLAST2 sequence comparison program may be downloaded from the National Center for Biotechnology Information's website or otherwise obtained from the National Institutes of Health, Bethesda, Md. NCBI-BLAST2 uses several search parameters, wherein all of those search parameters are set to default values including, for example, unmask=yes, strand=all, expected occurrences=10, minimum low complexity length=15/5, multi-pass e-value=0.01, constant for multi-pass=25, dropoff for final gapped alignment=25.

The method of the invention may include measuring an amount of expression of one small non-coding RNA or a combination of the small non-coding RNAs described above.

The small non-coding RNA is typically found in a biological sample from the patient. As used herein, a biological sample refers to any sample obtained from a patient. Exemplary biological samples include blood, urine, a tissue sample from any organ, and/or tissue sample from the transplanted organ. Urine samples are preferred.

Reference Amount of Expression of the Small Non-Coding Marker RNA

The method further includes comparing the measured amount of expression of the small non-coding marker RNA in the biological sample from the patient to a reference amount of expression of the small non-coding marker RNA.

In one embodiment, the reference amount of expression of the small non-coding marker RNA may be obtained by measuring an amount of expression of the small non-coding RNA in a person having a non-rejected organ. For example, the person having a non-rejected organ includes a healthy person. Preferably, the healthy person is a person of similar age, gender, race, graft-donor source, Banff histologic grade, and/or underwent the same initial anti-rejection treatment as the patient having a transplanted organ for which risk of organ failure is to assessed.

Another example of a person having a non-rejected organ is a person having a well-functioning (e.g., stable) transplanted organ. A well-functioning (e.g., stable) transplanted organ may be defined as a transplanted organ that does not exhibit organ failure (e.g., rejection). Preferably, a well-functioning transplanted organ is a transplanted organ that has not developed transplant dysfunction or morphologic evidence of transplant injury in areas of the transplant. For example, a stable functioning kidney transplant may be defined as having a serum creatinine concentration that has not changed by more than approximately 0.2 mg per deciliter during the seven days before and the seven days after collection of the biologic specimen for measurements of the small non-coding RNA. Preferably, the person having a well-functioning (e.g., stable) transplanted organ is a person of similar age, gender, race, graft-donor source, Banff histologic grade, and/or underwent the same initial anti-rejection treatment as the patient having a transplanted organ for which risk of organ failure is to assessed.

In another embodiment, the reference amount is obtained by measuring an amount of expression of said small non-coding RNA in a second biological sample from the patient. For example, the second biological sample may be obtained from the patient before the organ transplantation and/or from another non-rejected organ of the patient.

In yet another embodiment, the reference amount of expression of the small non-coding RNA is a value for expression of the small non-coding RNA that is accepted in the art.

Comparing the Measured Amount of Expression of the Small Non-Coding Marker RNA

The method includes comparing the measured amount of expression of the small non-coding RNA to the reference amount of expression of the small non-coding RNA. The small non-coding marker RNA may be, for example, a small non-coding RNA selected from SEQ ID NOs: 1-53, or variants thereof. Preferably the small non-coding marker RNA is selected from SEQ ID NOs 1: 49, or variants thereof.

In a more preferred embodiment, the small non-coding marker RNA is selected from a sequence set forth in SEQ ID NOs: 1-9, or a variation thereof. For example, the small non-coding marker RNA includes a small non-coding RNA selected from miR-142-5p; miR-142-3p; miR-155; miR-223; miR-146a; miR-146b; miR-342; miR-650; miR-21; and/or miR-425-5p, or a combination thereof, wherein an increase of expression of the small non-coding marker RNA that is equivalent to at least about 1-fold as compared to the reference amount of expression of the small non-coding marker RNA indicates an increased risk of rejection of the transplanted organ. In a most preferred embodiment, the small non-coding marker RNA is miR-142-5p; miR-142-3p; and/or miR-155.

An increase of expression that is equivalent to at least about 1-fold may be an increase in an amount equivalent to at least about 1-, 2-, 3-, 4-, 5-, 6-, 7-, 8-, 9-, 10-, 11-, 12-, 13-, 14-, 15-, 16-, 17-, 18-, 19-, 20-fold, or more as compared to the increase in the reference amount of expression of the small non-coding marker RNA. Preferably, the increase is a fold value. Examples of methods to quantify an increase of expression are known in the art, as are described in the General Methods section below.

An increased risk of organ rejection varies in different patients and the type of organ transplanted. Generally, the increased risk is at least about 25%, at least about 50%, at least about 75%, or at least about 90% as compared to a person having no risk of organ rejection.

Conversely, in one embodiment, an increase of expression of the small non-coding marker RNA selected from a sequence set forth in SEQ ID NOs: 1-9, or a variation thereof, that is equivalent to about less than 1-fold, as compared to the reference amount of expression of the small non-coding marker RNA, indicates a decreased risk of rejection of the transplanted organ. The decreased risk of organ rejection varies in different patients and the type of organ transplanted. Generally, the decreased risk is at least about 25%, at least about 50%, at least about 75%, or at least about 90% as compared to a person having no risk of organ rejection.

In another preferred embodiment, the small non-coding marker RNA is selected from a sequence set forth in SEQ ID NOs: 10-49, or a variation thereof. For example, the small non-coding marker RNA includes a small non-coding RNA selected from miR-30c; miR-30a-3p; miR-10a; miR-30e-3p; miR-30b; miR-10b; miR-32; miR-9; miR-193b; miR-143; miR-489; miR-27b; miR-126; miR-378; miR-429; miR-181c; miR-196b; miR-199a; miR-660; miR-203; miR-204; miR-30e-5p; miR-30a-5p; miR-30d; miR-125b; miR-130a; miR-126; miR-195; miR-26a; miR-26b; miR-497; miR-152; miR-141; miR-296; miR-365; miR-99a; miR-100; miR-186; and/or let-7a, wherein an increase of expression of the small non-coding RNA that is equivalent to less than 1-fold as compared to the reference amount of expression of the small non-coding marker RNA indicates an increased risk of rejection of the transplanted organ.

An increase of expression that is equivalent to less than 1-fold may be an increase of at most about 0.9-, 0.8-, 0.7-, 0.6-, 0.5-, 0.4-, 0.3-, 0.2-, or 0.1-fold, or less as compared to the increase in the reference amount of expression of the small non-coding marker RNA. Preferably, the increase is a fold value. Examples of methods to quantify an increase of expression are known in the art, as are described in the General Methods section below.

Conversely, in one embodiment, an increase of expression of the small non-coding marker RNA selected from a sequence set forth in SEQ ID NOs: 10-49, or a variation thereof, equivalent to at least about 1-fold, or more, as compared to the reference amount of expression of the small non-coding marker RNA, indicates a decreased risk of rejection of the transplanted organ. The decreased risk of organ rejection varies in different patients and the type of organ transplanted. Generally, the decreased risk is at least about 25%, at least about 50%, at least about 75%, or at least about 90% as compared to a person having no risk of organ rejection.

Use of an Endogenously Expressed Small Non-Coding Reference RNA to Further Indicate an Increased Risk of Organ Rejection Measuring and Comparing an Amount of an Endogenously Expressed Small Non-Coding Reference RNA In yet another embodiment, the method for assessing risk of organ rejection further includes measuring an amount of an endogenously expressed small non-coding reference RNA in a biological sample from the patient. In addition, the method includes measuring a reference amount of an endogenously expressed small non-coding reference RNA in a biological sample.

The reference amount may be obtained by measuring the amount of expression of the endogenously expressed small non-coding reference RNA in a person having a non-rejected organ or in a second biological sample from the patient, as described above. In another embodiment, the reference amount is a value for expression of the endogenously expressed small non-coding reference RNA that is accepted in the art.

An endogenously expressed small non-coding reference RNA refers to a small non-coding RNA that is endogenously expressed (e.g., expressed within the patient, cell, and/or tissue) and demonstrates an expression that is relatively constant and abundant in the biological sample.

Methods of selecting and validating the endogenously expressed small non-coding reference RNA are known in the art. See, for example, TaqMan® MicroRNA Assays from Applied Biosystems. Preferably, the endogenously expressed small non-coding reference RNA is stable, has a similar size as the measured small non-coding RNA (e.g., SEQ ID NOs: 1-53), and is amenable to means for measuring expression.

Examples of endogenously expressed small non-coding reference RNA include RNU24, RNU66, RNU19, RNU38B, RNU49, Z30, RNU6B, RNU48, RNU43, and/or RNU44. Preferably, the endogenously expressed small non-coding reference RNA is endogenous small nucleolar RNA RNU44.

Measuring a Difference in Expression of Marker RNA to Reference RNA

In a preferred embodiment, the method further includes measuring a difference between the amount of expression of the small non-coding marker RNA in the biological sample and the reference amount of expression of the small non-coding marker RNA. For example, the method can include measuring the difference between the amount of expression of the small non-coding marker RNA in the biological sample from the patient and the reference amount of expression of the small non-coding marker RNA.

As explained above, the reference amount may be obtained by measuring the amount of expression of the endogenously expressed small non-coding reference RNA in a person having a non-rejected organ or in a second biological sample from the patient, as described above. In another embodiment, the reference amount is a value for expression of the endogenously expressed small non-coding reference RNA that is accepted in the art.

The embodiment further includes measuring a difference between the amount of expression of the endogenously expressed small non-coding reference RNA in the biological sample and the reference amount of expression of the endogenously expressed small non-coding reference RNA. Or example, the method includes measuring the difference between the amount of expression of the endogenously expressed small non-coding reference RNA in the biological sample from the patient and the reference amount of expression of the endogenously small non-coding reference RNA.

As explained above, the reference amount may be obtained by measuring the amount of expression of the endogenously expressed small non-coding reference RNA in a person having a non-rejected organ or in a second biological sample from the patient, as described above. In another embodiment, the reference amount is a value for expression of the endogenously expressed small non-coding reference RNA that is accepted in the art.

The embodiment further includes comparing (i) the difference in amount of expression of the small non-coding marker RNA between the patient sample and the reference amount and (ii) the difference in amount of expression of the endogenously expressed small non-coding reference RNA between the patient sample and the reference amount. When the difference in (i) (i.e., expression of the small non-coding marker RNA between the patient sample and the reference amount) is greater than the difference in (ii) (i.e., the amount of expression of the endogenously expressed small non-coding reference RNA between the patient sample and the reference amount), the comparison further indicates an increased risk of rejection of the transplanted organ.

Preferably, a difference in (i) that is greater than the difference in (ii) by an amount equivalent to at least about 1-, 2-, 3-, 4-, 5-, 6-, 7-, 8-, 9-, 10-, 11-, 12-, 13-, 14-, 15-, 16-, 17-, 18-, 19-, 20-fold, or more, indicates an increased risk of rejection of the transplanted organ.

In another preferred embodiment, a difference in (i) that is greater than the difference in (ii) by an amount equivalent to less than 1-fold, for example, at most about 0.9-, 0.8-, 0.7-, 0.6-, 0.5-, 0.4-, 0.3-, 0.2-, or 0.1-fold, or less, indicates an increased risk of rejection of the transplanted organ.

Accordingly, the present embodiment relates to one example by which one skilled in the art may measure and/or determine whether the increase in expression of the small non-coding RNA, as compared to the reference amount, is statistically significant in the patient.

Normalizing

In a preferred embodiment, the invention includes normalizing the amount of expression of the small non-coding marker RNA. The method includes measuring an amount of expression of a small non-coding marker RNA in a biological sample from the patient, as described above. The method further includes measuring an amount of expression of an endogenously expressed small non-coding reference RNA in a biological sample from the patient. In addition, the method includes comparing the measured amount of the small non-coding marker RNA from the patient to the measured amount of endogenously expressed small non-coding reference RNA from the patient to determine a first ratio.

The method further includes measuring an amount of expression of the small non-coding marker RNA in a biological sample from a person having a non-rejected organ. The method further includes measuring an amount of expression of an endogenously expressed small non-coding reference RNA in a biological sample from the person having a non-rejected organ. In addition, the method includes comparing the measured amount of the small non-coding marker RNA from the person having a non-rejected organ to the measured amount of endogenously expressed small non-coding reference RNA from the person having a non-rejected organ to determine a second ratio.

When a calculation of the first ratio is greater than the second ratio by an amount equivalent to at least 1-fold, the calculation indicates an increased risk of rejection of said transplanted organ in the patient having a transplanted organ. The calculated increase of the first ratio over the second ratio that is at least 1-fold may be an increase that is equivalent to at least about 1-, 2-, 3-, 4-, 5-, 6-, 7-, 8-, 9-, 10-, 11-, 12-, 13-, 14-, 15-, 16-, 17-, 18-, 19-, 20-fold, or more.

When a calculation of the first ratio is greater than the second ratio by an amount equivalent to less than 1-fold, the calculation indicates an increased risk of rejection of said transplanted organ in the patient having a transplanted organ. The calculated increase of the first ratio over the second ratio may be an increase that is equivalent to less than 1-fold may be an increase of at most about 0.9-, 0.8-, 0.7-, 0.6-, 0.5-, 0.4-, 0.3-, 0.2-, or 0.1-fold, or less.

Accordingly, in the present embodiment, fold changes or equivalents thereof for the small non-coding marker RNA are normalized to the endogenously expressed small non-coding reference RNA.

Serum Creatinine and Additional Embodiments

In one embodiment, when the transplanted organ is a kidney, the method for assessing risk of organ rejection in a patient may further include determining the amount of serum creatinine protein in the patient. The determination of the amount of serum creatinine can be made by any method known to those skilled in the art, such as those described in U.S. Patent Publication US20080131441, which is incorporated by reference herein.

In this embodiment, the measured amount of serum creatinine in the patient is compared to a control amount of serum creatinine of a healthy person or a person having a well-functioning (e.g., stable) transplant, as described in U.S. Patent Publication 20080131441, which is incorporated by reference herein. For example, the normal level of serum creatinine in a healthy person or a person with a well-functioning transplant is generally about 0.8-1.6 milligrams/deciliter. The person may be the patient or a person different from the patient.

It is not necessary to determine the level of creatinine in a control sample every time the method is conducted. For example, the serum creatinine level from the patient can be compared to that of one or more previously determined control samples or to a level recognized by the physician or clinician conducting the method, or by a consensus of medical and/or clinical practitioners.

In another embodiment, the method further includes informing the patient whether the patient is at decreased or increased risk of organ rejection. The information that a patient is at risk of rejection of a transplanted organ is useful. Such patients can be prescribed and/or administered a treatment to prevent rejection and/or loss of the transplanted organ.

In one embodiment, the treatment includes administering to the patient an effective amount of a pharmaceutical composition to prevent rejection and/or loss of the transplanted organ. Such pharmaceutical compositions are well known to those skilled in the art, and include, for example a steroid pulse, an antibody, etc.

For example, a steroid pulse therapy can include the administration for three to six days of a high dose corticosteroid (e.g., greater than 100 mg). An example of an antibody therapy includes the administration for seven to fourteen days of the polyclonal antibody Thymoglobin or the monoclonal antibody, OKT3.

Another example of a treatment that can be administered is plasmapheresis. Plasmapheresis is a process in which the fluid part of the blood (i.e., plasma) is removed from blood cells. Typically, the plasma is removed by a device known as a cell separator. The cells are generally returned to the person undergoing treatment, while the plasma, which contains antibodies, is discarded.

Each of the methods and embodiments of the present invention can be used alone, or in combination with one or more, or all, of the other methods.

General Methods

A biological sample from a patient or person can be obtained by any method known to those in the art. In addition to the examples described above, further examples of biological samples include transplant tissue biopsy, blood, urine, bile, bronchioalveolar lavage fluid, and pericardial fluid. Suitable methods include, for example, venous puncture of a vein to obtain a blood sample, collection of a urine specimen, and a percutaneous core needle biopsy.

Any method known to those in the art can be employed for determining the amount of a small non-coding RNA. Typically, total RNA is isolated from the biological sample. RNA can be isolated from the sample by any method known to those in the art. For example, commercial kits, such as the TRI Reagent® commercially available from Molecular Research Center, Inc. (Cincinnati, Ohio), or the mirVana miRNA isolation kit from Ambion, can be used to isolate RNA. The yield and purity of RNA can be measured using a NanoDrop ND-1000 spectrophotometer.

The quantification of small non-coding RNA from total mRNA from the biological sample can be performed by any method known to those in the art. For example, kinetic, quantitative PCR involves reverse transcribing the total RNA (e.g., by using the Taqman Multiplex RT set for TaqMan Array Human MicroRNA Panel v1.0) and polymerase chain reaction (PCR). Quantitative PCR can be carried out on an Applied BioSystems 7900HT thermocycler, or an equivalent thereof, using the manufacturer's recommended cycling conditions. Briefly, cDNA can be reverse transcribed from the total RNA samples using specific small non-coding RNA primers, which may be obtained from the TaqMan MicroRNA assays (Applied Biosystems) and reagents from the TaqMan microRNA reverse transcription kit (Applied Biosystems).

Generally, the isolated small non-coding RNA may be amplified by methods known in the art. Amplification systems utilizing, for example, PCR or RT-PCR methodologies are known to those skilled in the art. For a general overview of amplification technology, see, for example, Dieffenbach et al., *PCR Primer: A Laboratory Manual*, Cold Spring Harbor Laboratory Press, New York (1995). For example, the amounts of small non-coding RNA can be determined using kinetic, quantitative PCR. Preferably, PCR products are amplified from cDNA samples using the TaqMan microRNA assay (Applied Biosystems).

An alternative method for determining the amount of small non-coding RNA expression includes the use of molecular beacons and other labeled probes useful in, for example multiplex PCR. In a multiplex PCR assay, the PCR mixture contains primers and probes directed to the small non-coding RNA PCR product. Typically, a single fluorochrome is used in the assay. The molecular beacon or probe is detected to determine the amount of small non-coding RNA. Molecular beacons are described, for example, by Tyagi and Kramer (Nature Biotechnology 14, 303-308, 1996) and by Andrus and Nichols in U.S. Patent Application Publication No. 20040053284.

Another method includes, for instance, quantifying cDNA (obtained by reverse transcribing the small non-coding RNA) using a fluorescence based real-time detection method, such as the ABI PRISM 7700 or 7900 Sequence Detection System [TaqMan®)] commercially available from Applied Biosystems, Foster City, Calif. or similar system as described by Heid et al., (*Genome Res.* 1996; 6:986-994) and Gibson et al. (*Genome Res.* 1996; 6:995-1001).

Small non-coding marker RNA copy numbers can then be normalized using an endogenously expressed small non-coding reference RNA copy number and the abundance of the small non-coding marker RNA can be expressed as a ratio of the small non-coding marker RNA to the endogenously expressed small non-coding reference RNA.

Generally, the amount of small non-coding RNA expression in a biological sample is significantly greater if the expression of small non-coding RNA is heightened. For example, a discriminatory level for heightened gene expression (e.g., the baseline magnitude of expression) of the small non-coding RNA is defined as the mean±95% confidence interval of a group of values observed in non-rejecting organs (e.g., control values, i.e., control levels). The group of values as used herein includes, for example, a minimum of at least about 2 values, more preferably a minimum of at least about 10 values, most preferably a minimum of at least about 20 values. The group of values as used herein includes, for example, a maximum of at most about 500 values, more preferably a maximum of at most about 100 values, most preferably a maximum of at most about 50 values.

Heightened expression of the small non-coding RNA is considered to be significantly greater if the value is greater than the mean±95% confidence interval of a group of values observed in non-rejecting organs. Similarly, the level of the small non-coding RNA in the cell sample is considered to be significantly lower if the amount of expression of the small non-coding RNA is lower than the mean±95% confidence interval of a group of values observed in non-rejecting organs.

The amount of expression of the small non-coding RNA is typically considered not significantly greater if the level of the small non-coding RNA in the biological sample is not greater than the mean±95% confidence interval of a group of values observed in non-rejecting organs. The amount of expression of the small non-coding RNA is normally considered not significantly lower if the amount in a biological sample is not lower than the mean±95% confidence interval of a group of values observed in nonrejecting transplants.

Statistical analysis in the above mean±95% confidence interval of a group of values observed in non-rejecting organs may be performed with a $x^2$ test.

In another embodiment, the amount of expression of the small non-coding marker RNA in a biological sample is significantly greater if the log-transformed mean (±SE) ratio of the small non-coding marker RNA copies to the endogenously expressed small non-coding reference RNA copies is higher relative to a control ratio in non-rejecting organs, as determined by the Kruskal-Wallis test. For example, a significantly greater ratio is typically at least about ±SE 3.0, more typically between ±SE 3.0 and 5.0, and most typically between ±SE 3.8 and 4.7.

Similarly, the amount of the small non-coding RNA in a biological sample is significantly lower if the log-transformed mean (±SE) ratio of the small non-coding marker RNA copies to the endogenously expressed small non-coding reference RNA copies is reduced relative to a control ratio (i.e., control values, control levels) in non-rejecting organs, as determined by the Kruskal-Wallis test. For example, a typical non-rejecting organ control ratio is not more than about 2.5, more typically 1.0 to 2.5, and most typically from 1.3 and 2.0.

In an embodiment of the invention, generally, the amount of small non-coding RNA when compared to a control amount may be increased by at least about 10%, at least about 50%, or at least about 100%. The amount of expression level of a small non-coding RNA when compared to a control amount may be decreased by at least about 10%, at least about 50%, or at least about 100% lower.

It is not necessary to determine the amount of expression of the small non-coding marker RNA or the endogenously expressed small non-coding reference RNA in a every time the method is conducted. For example, the amount of small non-coding marker or reference RNA in the biological sample from the transplanted organ can be compared to that of one or more previously determined control samples or compared to an amount recognized by the physician or clinician conducting the method of a consensus of medical and/or clinical practitioners.

With respect to serum creatinine, any method known in the art can be used for determining the amount of serum creatinine in the biological sample. Suitable methods for determining protein levels include an ELISA and a standard blot. Briefly, these assays are normally based on incubating an antibody specific to the protein with a sample suspected of containing the protein, and detecting the presence of a complex between the antibody and the protein.

Alternatively, commercial kits can be utilized. An example of a commercial kit for determining creatinine level is the QuantiChrom™ Creatinine Assay Kit from BioAssay Systems (Hayward, Ca).

Kit

In another aspect, the invention relates to a kit for assessing risk of organ rejection in a patient having a transplanted organ. The kit includes at least one nucleic acid molecule complementary to a small non-coding marker RNA selected from SEQ ID NOs: 1-49, or variations thereof. The kit further includes a means for measuring expression of a small non-coding marker RNA in a biological sample. The kit may also include written instructions for a method of assessing risk of organ rejection, as described above.

In a preferred embodiment, the means for measuring expression includes quantitative polymerase chain reaction. Additional means for measuring expression include those described under General Methods.

EXAMPLES

Example 1

MicroRNA Expression Profiles of Human Renal Allografts. We first determined global miRNA expression profiles of human renal allografts using microfluidic cards containing TaqMan primers and probes for 365 mature human miRNAs. The characteristics of patients whose renal allograft biopsies were studied for global miRNA expression patterns (training set), or for a subset of differentially expressed miRNAs (validation set), are summarized in Table 1.

Among the 365 mature human miRNAs analyzed in the training set (4 normal and 3 AR biopsies), 174±7 miRNAs (48%) were expressed in each biopsy sample (174±10 miRNAs in the AR biopsies vs. 174±4 miRNAs in the normal allograft biopsies). Unsupervised hierarchical clustering of miRNA expression patterns correctly classified the normal allograft biopsies and the AR biopsies (FIG. 1A).

The clear separation of AR biopsies from normal allograft biopsies was further confirmed by displaying the relationships among miRNA expression patterns using principal component analysis (PCA) (FIG. 1B). Samples were accurately grouped by PC1, which explained 46% of the overall miRNA expression variability, whereas PC2 explained 21% of the variability and did not classify the samples according to their diagnosis. Table 2 below lists the miRNAs with high contribution to the overall variability of the samples.

TABLE 2

Squared cosines table of miRNAs corresponding to their contribution to the grouping of the samples by the principal component analysis

| MicroRNA | |
|---|---|
| | PC1 |
| hsa-miR-26a | 0.949 |
| hsa-miR-30d | 0.944 |
| hsa-miR-200a | 0.937 |
| hsa-miR-660 | 0.933 |
| hsa-miR-23b | 0.928 |
| hsa-miR-32 | 0.921 |
| hsa-miR-30a-3p | 0.920 |
| hsa-miR-125a | 0.914 |
| hsa-miR-26b | 0.913 |
| hsa-miR-10a | 0.908 |
| hsa-miR-30c | 0.903 |
| hsa-miR-30e-3p | 0.901 |
| hsa-miR-10b | 0.896 |
| hsa-miR-30b | 0.883 |
| hsa-miR-152 | 0.882 |
| hsa-let-7c | 0.862 |
| hsa-miR-30a-5p | 0.858 |
| hsa-miR-196b | 0.852 |
| hsa-miR-489 | 0.851 |
| hsa-miR-186 | 0.830 |
| hsa-miR-151 | 0.817 |
| hsa-miR-125b | 0.816 |
| hsa-miR-532 | 0.811 |
| hsa-miR-101 | 0.806 |
| hsa-miR-141 | 0.800 |
| hsa-miR-130a | 0.796 |
| hsa-miR-30e-5p | 0.784 |

TABLE 2-continued

Squared cosines table of miRNAs corresponding to their contribution to the grouping of the samples by the principal component analysis

| MicroRNA | |
|---|---|
| hsa-miR-195 | 0.781 |
| hsa-miR-429 | 0.775 |
| hsa-miR-24 | 0.769 |
| | PC2 |
| hsa-miR-93 | 0.903 |
| hsa-miR-15b | 0.853 |
| hsa-miR-425-5p | 0.829 |
| hsa-miR-16 | 0.754 |
| hsa-miR-28 | 0.728 |
| hsa-miR-565 | 0.631 |
| hsa-miR-155 | 0.600 |
| hsa-miR-320 | 0.586 |
| hsa-miR-191 | 0.577 |
| hsa-miR-103 | 0.563 |
| hsa-miR-146a | 0.561 |
| hsa-miR-342 | 0.550 |
| hsa-miR-146b | 0.538 |
| hsa-let-7d | 0.525 |
| hsa-miR-142-5p | 0.504 |
| hsa-miR-594 | 0.492 |
| hsa-miR-142-3p | 0.476 |
| hsa-miR-181d | 0.464 |
| hsa-miR-127 | 0.463 |
| hsa-miR-106b | 0.409 |
| hsa-miR-130b | 0.392 |
| hsa-miR-95 | 0.391 |
| hsa-miR-21 | 0.352 |
| hsa-miR-223 | 0.341 |
| hsa-miR-25 | 0.335 |
| hsa-miR-451 | 0.327 |
| hsa-miR-486 | 0.318 |
| hsa-let-7 g | 0.310 |
| hsa-miR-345 | 0.303 |
| hsa-miR-190 | 0.301 |

Example 2

Figure 2:
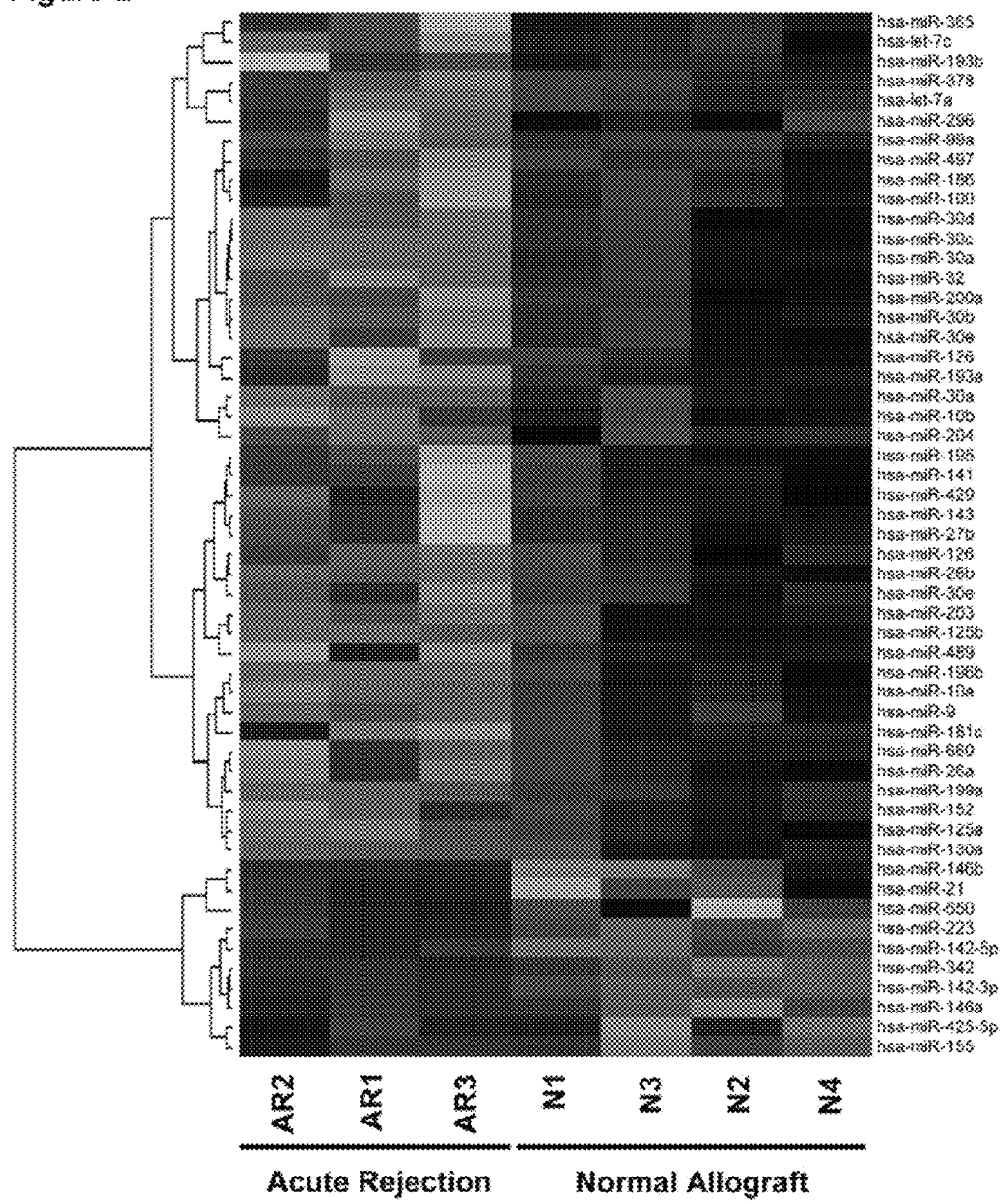
FIG. 2. Differential expression of miRNAs in acute rejection biopsies and normal allograft biopsies at a P value<0.05. MicroRNA (miRNA) expression patterns of 7 human kidney allograft biopsies [3 showing histological features of acute rejection (AR) and 4 with normal allograft biopsy results (N)] were examined using microfluidic cards containing TaqMan probes and primer pairs for 365 human mature miRNAs. Each column corresponds to the expression profile of a renal allograft biopsy, and each row corresponds to a miRNA. ABqPCR software was used to identify miRNAs that were differentially expressed between AR biopsies and normal allograft biopsies. $C_T$ filtering procedure was first performed. Assays with a $C_T$ value>35 in >50% of samples in each group were called undetected. Assays not detected in both groups were not included in the analysis. For the remaining assays, t test was used to detect differentially expressed miRNAs. The miRNA clustering tree is shown on the Left. Branch lengths represent the degree of similarity between individual miRNAs. The higher intensities of red mean higher expression level.

MicroRNAs Distinguishing Acute Rejection Biopsies from Normal Allograft Biopsies. Supervised analysis was used to detect miRNAs differentially expressed in AR biopsies and normal allograft biopsies. A subset of 17 miRNAs was differentially expressed at a P value<0.01. Among the 17 miRNAs, 10 (let-7c, miR-10a, miR-10b, miR-125a, miR-200a, miR-30a-3p, miR-30b, miR-30c, miR30e-3p, and miR-32) were underexpressed in AR biopsies compared to normal allograft biopsies, and 7 (miR-142-5p, miR-142-3p, miR-155, miR-223, miR-146b, miR-146a, and miR-342) were overexpressed (FIG. 2 and Table 3). At a P value<0.05, 33 additional miRNAs were found to be underexpressed in AR biopsies compared to normal allograft biopsies, and only 3 miRNAs were found to be overexpressed (FIG. 2 and Table 3).

TABLE 3

Differential expression of microRNAs in human renal allografts*

| miRNA | Target Sequence | SEQ ID NO: | Mean fold | P value † |
|---|---|---|---|---|
| Overexpressed in AR | | | | |
| hsa-miR-142-5p | CAUAAAGUAGAAAGCACUAC | 1 | 18.48 | <0.01 |
| hsa-miR-142-3p | UGUAGUGUUUCCUACUUUAUGGA | 2 | 16.61 | <0.01 |
| hsa-miR-155 | UUAAUGCUAAUCGUGAUAGGGG | 3 | 14.53 | <0.01 |
| hsa-miR-223 | UGUCAGUUUGUCAAAUACCCC | 50 | 9.20 | <0.01 |
| hsa-miR-146a | UGAGAACUGAAUUCCAUGGGUU | 4 | 3.65 | <0.01 |

TABLE 3-continued

Differential expression of microRNAs in human renal allografts*

| miRNA | Target Sequence | SEQ ID NO: | Mean fold | P value † |
|---|---|---|---|---|
| hsa-miR-146b | UGAGAACUGAAUUCCAUAGGCU | 5 | 2.90 | <0.01 |
| hsa-miR-342 | UCUCACACAGAAAUCGCACCCGUC | 6 | 2.90 | <0.01 |
| hsa-miR-650 | AGGAGGCAGCGCUCUCAGGAC | 7 | 11.31 | <0.05 |
| hsa-miR-21 | UAGCUUAUCAGACUGAUGUUGA | 8 | 3.45 | <0.05 |
| hsa-miR-425-5p | AAUGACACGAUCACUCCCGUUGA | 9 | 2.13 | <0.05 |
| Underexpressed in AR | | | | |
| hsa-miR-30c | UGUAAACAUCCUACACUCUCAGC | 10 | 0.31 | <0.01 |
| hsa-miR-30a-3p | CUUUCAGUCGGAUGUUUGCAGC | 11 | 0.32 | <0.01 |
| hsa-miR-10a | UACCCUGUAGAUCCGAAUUUGUG | 12 | 0.34 | <0.01 |
| hsa-miR-30e-3p | CUUUCAGUCGGAUGUUUACAGC | 13 | 0.36 | <0.01 |
| hsa-miR-30b | UGUAAACAUCCUACACUCAGCU | 14 | 0.40 | <0.01 |
| hsa-miR-125a | UCCCUGAGACCCUUUAACCUGUG | 52 | 0.41 | <0.01 |
| hsa-miR-10b | UACCCUGUAGAACCGAAUUUGU | 15 | 0.42 | <0.01 |
| hsa-miR-32 | UAUUGCACAUUACUAAGUUGC | 16 | 0.46 | <0.01 |
| hsa-let-7c | UGAGGUAGUAGGUUGUAUGGUU | 51 | 0.48 | <0.01 |
| hsa-miR-200a | UAACACUGUCUGGUAACGAUGU | 53 | 0.50 | <0.01 |
| hsa-miR-9 | UCUUUGGUUAUCUAGCUGUAUGA | 17 | 0.20 | <0.05 |
| hsa-miR-193b | AACUGGCCCUCAAAGUCCCGCUUU | 18 | 0.24 | <0.05 |
| hsa-miR-143 | UGAGAUGAAGCACUGUAGCUCA | 19 | 0.26 | <0.05 |
| hsa-miR-489 | AGUGACAUCACAUAUACGGCAGC | 20 | 0.26 | <0.05 |
| hsa-miR-27b | UUCACAGUGGCUAAGUUCUGC | 21 | 0.32 | <0.05 |
| hsa-miR-126‡ | CAUUAUUACUUUUGGUACGCG | 22 | 0.35 | <0.05 |
| hsa-miR-193a | AACUGGCCUACAAAGUCCCAG | 23 | 0.35 | <0.05 |
| hsa-miR-378 | CUCCUGACUCCAGGUCCUGUGU | 24 | 0.35 | <0.05 |
| hsa-miR-429 | UAAUACUGUCUGGUAAAACCGU | 25 | 0.36 | <0.05 |
| hsa-miR-181c | AACAUUCAACCUGUCGGUGAGU | 26 | 0.36 | <0.05 |
| hsa-miR-196b | UAGGUAGUUUCCUGUUGUUGG | 27 | 0.40 | <0.05 |
| hsa-miR-199a | CCCAGUGUUCAGACUACCUGUUC | 28 | 0.40 | <0.05 |
| hsa-miR-660 | UACCCAUUGCAUAUCGGAGUUG | 29 | 0.40 | <0.05 |
| hsa-miR-203 | GUGAAAUGUUAGGACCACUAG | 30 | 0.43 | <0.05 |
| hsa-miR-204 | UUCCCUUUGUCAUCCUAUGCCU | 31 | 0.43 | <0.05 |
| hsa-miR-30e-5p | UGUAAACAUCCUUGACUGGA | 32 | 0.43 | <0.05 |
| hsa-miR-30a-5p | UGUAAACAUCCUCGACUGGAAG | 33 | 0.44 | <0.05 |
| hsa-miR-30d | UGUAAACAUCCCCGACUGGAAG | 34 | 0.44 | <0.05 |
| hsa-miR-125b | UCCCUGAGACCCUAACUUGUGA | 35 | 0.45 | <0.05 |
| hsa-miR-130a | CAGUGCAAUGUUAAAAGGGCAU | 36 | 0.48 | <0.05 |
| hsa-miR-126‡ | UCGUACCGUGAGUAAUAAUGC | 37 | 0.48 | <0.05 |
| hsa-miR-195 | UAGCAGCACAGAAAUAUUGGC | 38 | 0.48 | <0.05 |
| hsa-miR-26a | UUCAAGUAAUCCAGGAUAGGC | 39 | 0.49 | <0.05 |
| hsa-miR-26b | UUCAAGUAAUUCAGGAUAGGUU | 40 | 0.49 | <0.05 |
| hsa-miR-497 | CAGCAGCACACUGUGGUUUGU | 41 | 0.51 | <0.05 |
| hsa-miR-152 | UCAGUGCAUGACAGAACUUGGG | 42 | 0.51 | <0.05 |
| hsa-miR-141 | UAACACUGUCUGGUAAAGAUGG | 43 | 0.52 | <0.05 |
| hsa-miR-296 | AGGGCCCCCCCUCAAUCCUGU | 44 | 0.52 | <0.05 |
| hsa-miR-365 | UAAUGCCCCUAAAAAUCCUUAU | 45 | 0.55 | <0.05 |
| hsa-miR-99a | AACCCGUAGAUCCGAUCUUGUG | 46 | 0.57 | <0.05 |
| hsa-miR-100 | AACCCGUAGAUCCGAACUUGUG | 47 | 0.62 | <0.05 |
| hsa-miR-186 | CAAAGAAUUCUCCUUUUGGGCUU | 48 | 0.62 | <0.05 |
| hsa-let-7a | UGAGGUAGUAGGUUGUAUAGUU | 49 | 0.67 | <0.05 |

*Differential expression of microRNAs in acute rejection (AR) biopsies (N = 3) compared to normal allograft biopsies (N = 4). The fold changes were calculated using the delta-delta $C_T$ method, using 1 of the normal biopsies as the calibrator. The mean fold presented corresponds to the ratio of acute rejection biopsy to normal allograft biopsy.
† P value calculated using Student's t test.
‡ Two sequences corresponding to miR-126 have been quantified in the microfluidic cards.

Example 3

Figure 3:
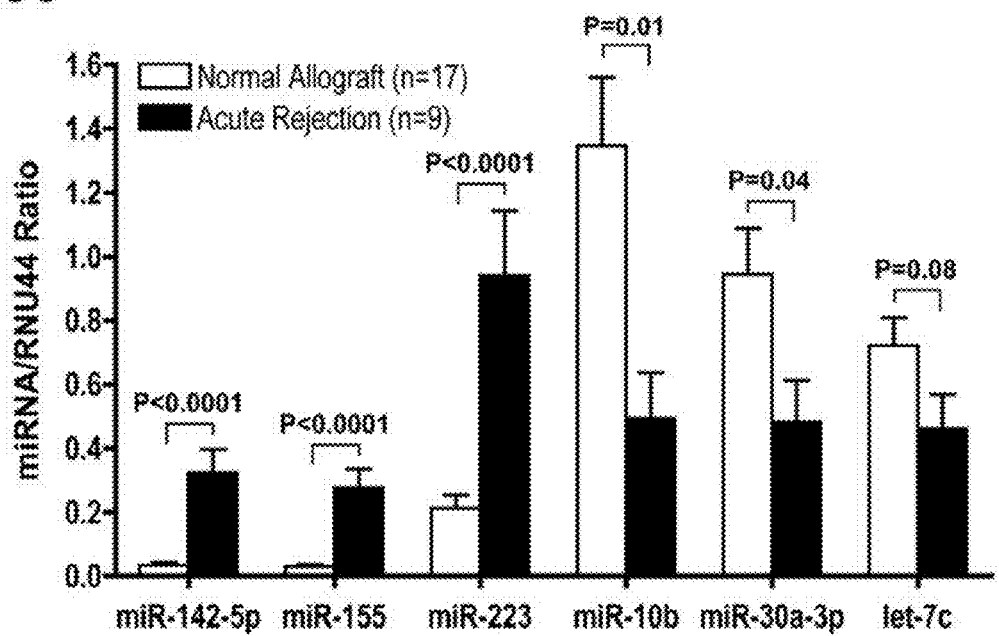
FIG. 3. Validation of differential expression of microRNAs in AR biopsies and normal allograft biopsies of human renal allografts. Intragraft expression levels of miR-142-5p, -155, -223, -10b, -30a-3p, and let-7c in an independent validation set of 9 acute rejection biopsies and 17 normal kidney allograft biopsies. Expression levels were quantified using modified TaqMan miRNA assays that allow absolute quantification of miRNAs. miRNA copy numbers were normalized using the stably expressed RNU44 small nucleolar RNA, and are shown as mean (±SE) ratio of miRNA copies to RNU44 copy numbers. RNU44 copy numbers were not different between the 9 acute rejection biopsies ($8.87 \times 10^6 \pm 1.48 \times 10^6$ copies/µg RNA) and the 17 normal allograft biopsies ($8.72 \times 10^6 \pm 8.42 \times 10^5$ copies/µg RNA, P=0.92). P value calculated using t test.

Validation of the MicroRNA Signatures Predictive of Renal Allograft Status. An independent set of 26 renal allograft biopsies (9 AR biopsies and 17 normal allograft biopsies) was used to validate a subset of miRNAs identified by global expression profiling to be differentially expressed in AR biopsies and normal allograft biopsies. FIG. 3 confirms the differential expression of miRNAs in AR biopsies compared to normal allograft biopsies. As observed in the training set, miR-142-5p (P<0.0001), -155 (P<0.0001), and -223 (P<0.0001) were overexpressed in AR biopsies in the validation set, and miR-10b (P=0.01), miR-30a-3p (P=0.04), and let-7C(P=0.08) were underexpressed.

Example 4

Intragraft mirRNA Levels Are Biomarkers of Renal Allograft Status. We investigated whether intragraft miRNA levels predict AR and renal allograft function. We used receiver-operating curves (ROCS) to analyze miRNA levels to determine cutoff points that yielded the highest combined sensitivity and specificity for predicting AR and allograft function. Our analysis showed that AR can be predicted very accurately using intragraft levels of miR-142-5p (100% sensitivity and 95% specificity, P<0.0001, Table 1) or miR-155 (100% sensitivity and 95% specificity, P<0.0001, Table 1). Intragraft levels of miR-223, -10b, -30a-3p, and let-7c were also diagnostic of AR but with a lesser level of accuracy (Table 1).

Analysis involving the ROC showed that AR can also be predicted using intragraft levels of T cell CD3 mRNA, B cell CD20 mRNA, and mRNA encoding renal tubular proteins NKCC-2 and USAG-1 but with much less sensitivity and specificity compared to intragraft levels of miR-142-5p, -155, or -223 (Table 1).

We examined whether intragraft miRNA levels predict renal allograft function. Renal graft function at the time of allograft biopsy was assessed by calculating glomerular filtration rate (eGFR) using the 4-parameter modified diet in renal disease (MDRD) formula. Our examination showed that intragraft levels of miR-142-5p (R=−0.66, P<0.0001), -10b (R=0.62, P<0.0001), -155 (R=−0.59, P=0.0003), -223 (R=−0.57, P=0.0006), -30a-3p (R=0.57, P=0.0006), and let-7c (R=0.37, P=0.03) are significantly associated with eGFR. Among the intragraft mRNAs assessed, CD3 mRNA ($R^2$=0.36, P=0.0002), but not mRNA for CD20 ($R^2$=0.04, P=0.25), NKCC-2 ($R^2$=0.01, P=0.58), or USAG-1 ($R^2$=0.08, P=0.21), was associated with graft function.

Example 5

Figure 4:
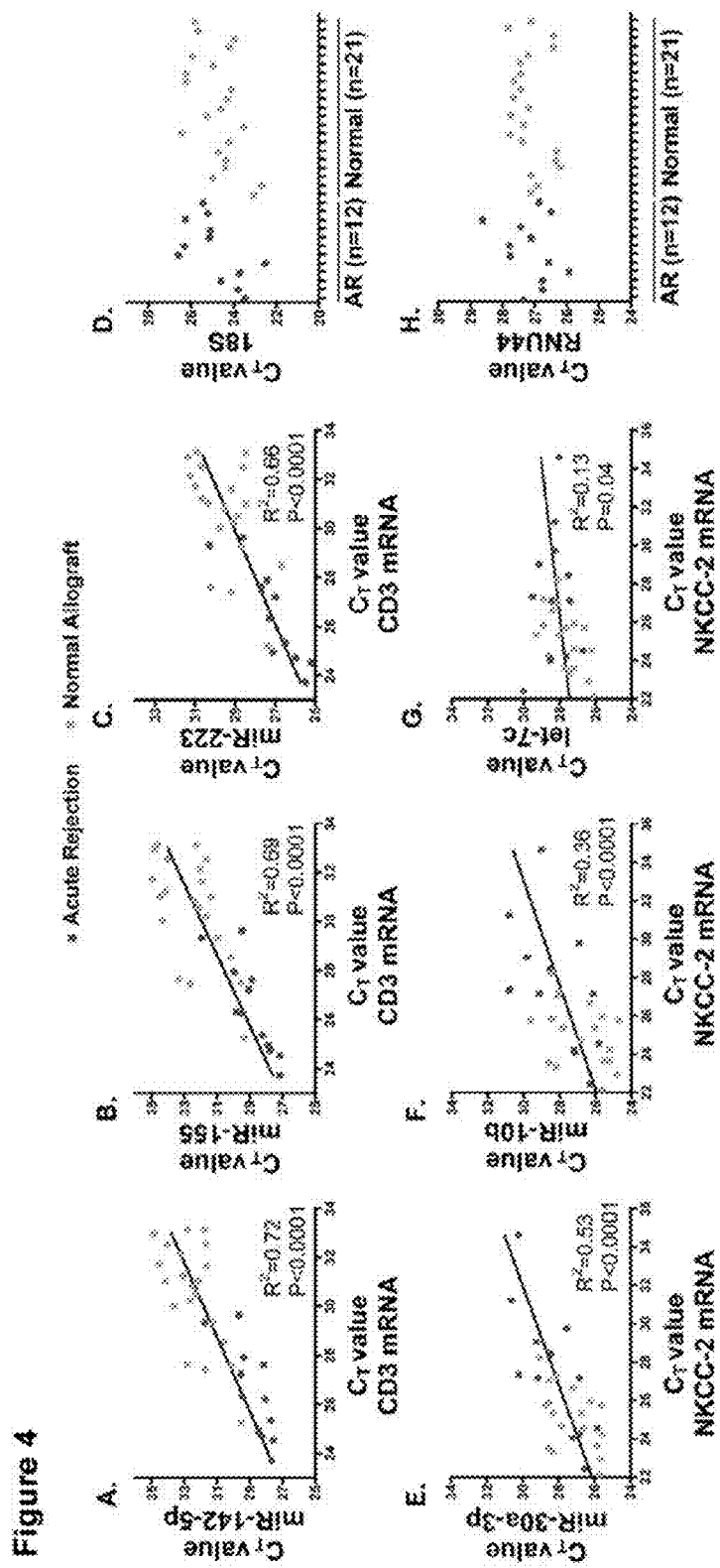
FIG. 4. Positive association between miRNAs and mRNAs in human allograft biopsies. Intragraft levels of miRNAs were quantified with the use of TaqMan miRNA assays, and intragraft levels of mRNAs were quantified using real time quantitative PCR assays, and the relationship between the intragraft levels of miRNA and mRNA is shown, along with Pearson correlation ($R^2$) and P values. A strong positive association between the levels of CD3 mRNA and the levels of miRNAs overexpressed in acute rejection biopsies was found: (A) miR-142-5p ($R^2$=0.72, P<0.0001); (B) miR-155 ($R^2$=0.69, P<0.0001); or (C) miR-223 ($R^2$=0.66, P<0.0001). A positive association between renal tubule specific NKCC-2 mRNA and miRNAs underexpressed in acute rejection biopsies was also observed: (E) miR-30a-3p ($R^2$=0.53, P<0.0001); (F) miR-10b ($R^2$=0.36, P<0.0001); or (G) let-7c ($R^2$=0.13, P=0.04). Results from all 33 renal allograft biopsies (red, 12 acute rejection biopsies; green, 21 normal allograft biopsies) are shown. The threshold cycle ($C_T$) is the fractional cycle number at which the fluorescence crossed the fixed threshold in miRNA/mRNA assays. (D) The mean (±SD) $C_T$ values of the endogenous control for mRNAs (18S rRNA, 24.8±1.3 vs. 24.7±1.1, P=0.86, t test) and (H) for miRNAs (RNU44 small nucleolar RNA, 27.1±0.7 vs. 27.1±0.5, P=0.97, t test) were similar between the acute rejection samples and the normal renal allografts.

Mechanisms for the Altered Intragraft Expression of miRNAs in AR Biopsies. FIG. 4 illustrates that there is a strong positive association between intragraft levels of CD3 mRNA and intragraft levels of miR-142-5p (FIG. 4A, $R^2$=0.72, P<0.0001), miR-155 (FIG. 4B, $R^2$=0.69, P<0.0001), or miR-223 (FIG. 4C, $R^2$=0.66, P<0.0001). We also found a strong positive relationship between intragraft levels of CD20 mRNA and miR-142-5p ($R^2$=0.61, P<0.0001), miR-155 ($R^2$=0.55, P<0.0001), or miR-223 ($R^2$=0.56, P<0.0001). In contrast, there was no association between renal tubule NKCC-2 mRNA or USAG-1 mRNA and miR-142-5p, -155, or miR-223 (all P values>0.05).

We examined whether an association exists between miRNAs underexpressed in AR biopsies and intragraft mRNA levels. We found a positive association between renal tubule-specific NKCC-2 mRNA and miR-30a-3p (FIG. 4E, $R^2$=0.53, P<0.0001), miR-10b (FIG. 4F, $R^2$=0.36, P<0.0001), or let-7c (FIG. 4G, $R^2$=0.13, P=0.04). In a similar fashion to NKCC-2, renal tubule-related USAG-1 mRNA levels were positively associated with the intragraft levels of miR-30a-3p ($R^2$=0.44, P<0.0001), miR-10b ($R^2$=0.35, P=0.0003), or let-7c ($R^2$=0.19, P=0.01). In contrast, there was no significant association between intragraft levels of CD3 mRNA or CD20 mRNA and miR-30a-3p, miR-10b, or let-7c (all P values>0.05).

Figure 5:
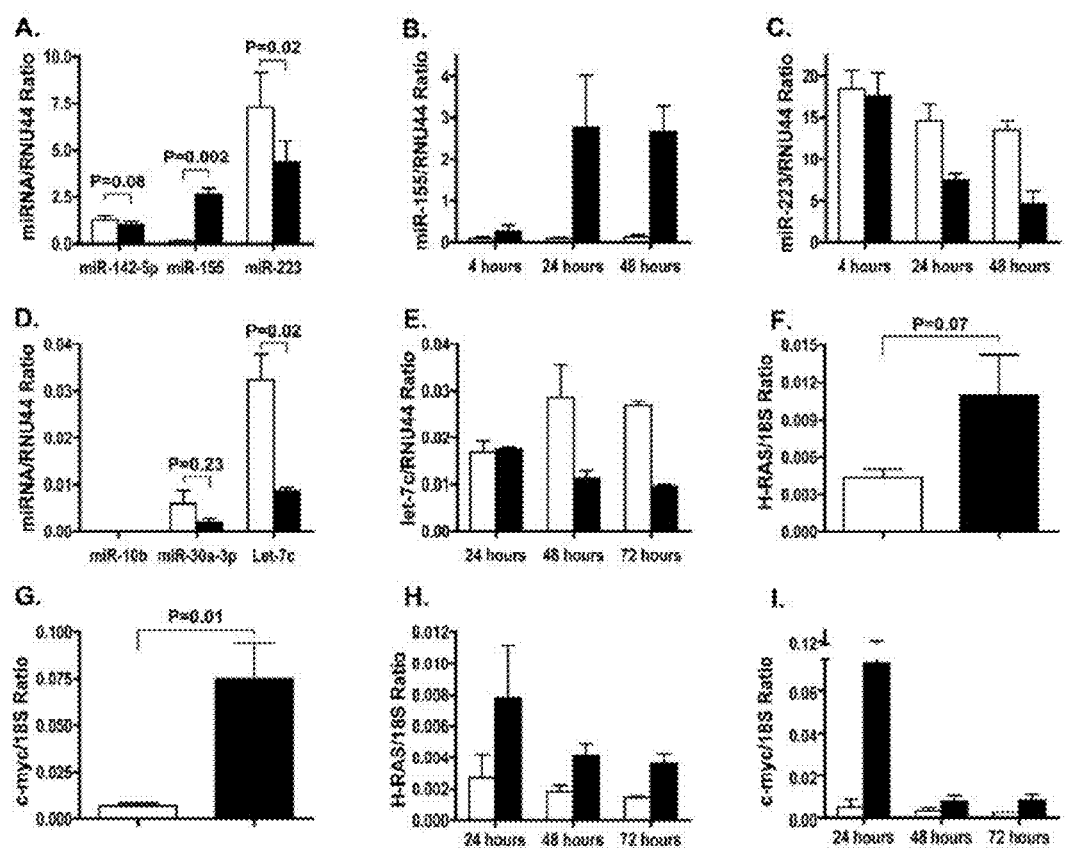
FIG. 5. Levels of miRNAs in resting or activated normal human peripheral blood mononuclear cells. Peripheral blood mononuclear cells (PBMCs) were obtained from healthy individuals and were incubated without (open bars) or with (filled bars) 2 µg/mL PHA for 24 h (A, F, and G) (n=7 subjects), 48 h (D) (n=4 subjects), or 24, 48, and 72 h (B, C, E, H, and I) (n=2 subjects), and RNA was isolated for miRNA quantification (A-E) or mRNA quantification (F-I). miRNA copy numbers were normalized using the RNU44 small nucleolar RNA copy numbers and mRNA copy numbers were normalized using the 18S rRNA copy numbers and are shown as mean (±SE) ratio of miRNA copies to RNU44 copy numbers or ratio of mRNA copies to 18S rRNA copies. P value calculated using paired t test.

To address whether the altered expression of miRNAs in AR biopsies is because of the relative proportions of graft-infiltrating immune cells and resident kidney parenchymal cells, we quantified the abundance of differentially expressed miRNAs in normal human PBMCs and in normal HRECs. We also investigated whether stimulation of PBMCs or HRECs altered the level of expression of miR-NAs. Our investigation showed that whereas the absolute levels of RNU44 small nucleolar miRNA was similar in both PBMCs and HRECs ($2.0 \times 10^7 \pm 1.2 \times 10^7$ vs. $2.35 \times 10^7 + 1.9 \times 10^6$, P>0.05), the miRNAs overexpressed in AR biopsies (miR-142-5p, miR-155, and miR-223) were all expressed at a higher level in normal human PBMCs compared to miR-NAs (miR-30a-3p, miR-10b, or let-7c) underexpressed in AR biopsies. Moreover, stimulation of PBMCs with the mitogen phytohaemagglutinin (PHA) results in an increase in the abundance of miR-155 (P=0.0002) and a decrease in miR-223 (P=0.02), let-7c (P=0.02), or miR-142-5p (P=0.08) (FIG. 5). H-ras and c-myc are targets of let-7c, and activation of PBMCs with PHA resulted in the increased expression of mRNAs for c-myc (P=0.01) and H-ras (P=0.07) (FIG. 5).

Figure 6:
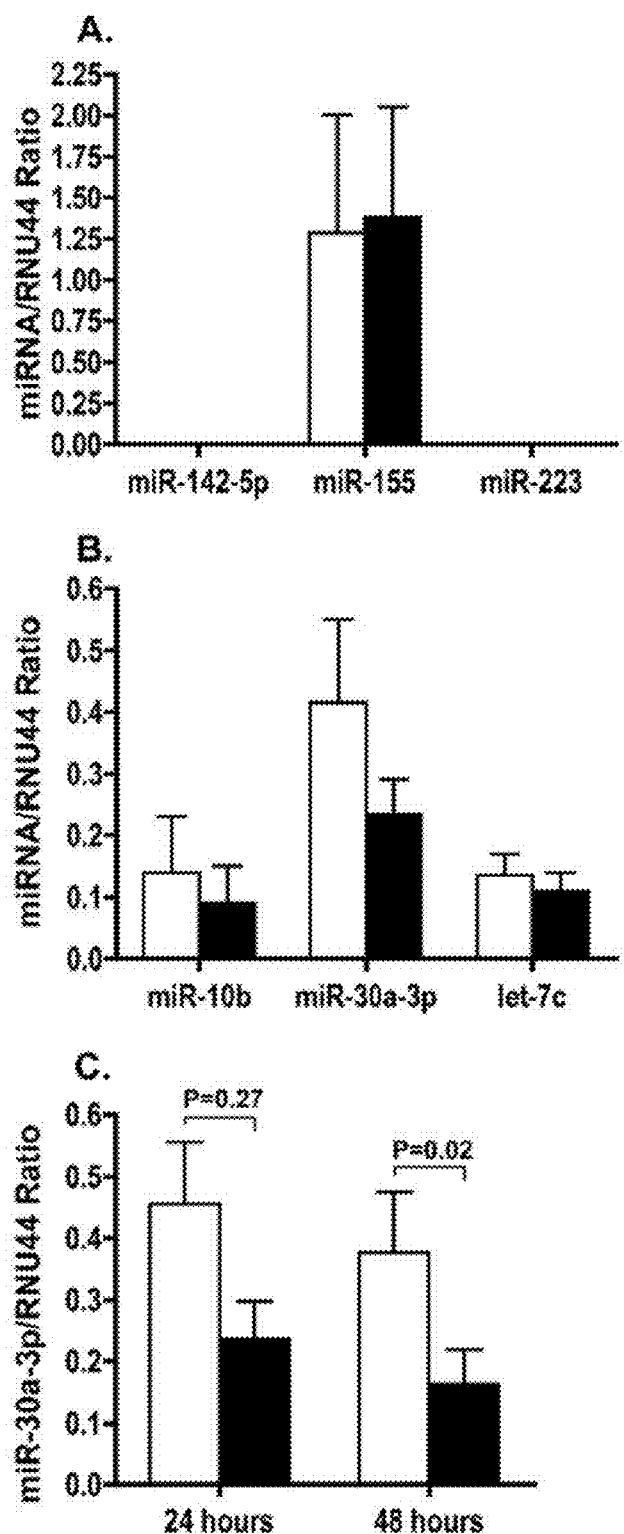
FIG. 6. Levels of miRNAs in resting or activated normal human renal epithelial cells. Primary cultures of normal human renal epithelial cells (HRECs) were incubated for 24 h (A, B) or 24 and 48 h (C) with cell-free supernatants of resting PBMCs (open bars) or cell-free supernatants of PBMCs activated with 2 µg/mL PHA (filled bars). Total RNA was isolated from HRECs and a subset of miRNAs found to be overexpressed (A) or underexpressed (B and C)

Quantification of miRNAs in primary cultures of HRECs showed that miR-30a-3p, miR-10b, or let-7c are expressed at a higher level in HRECs compared to PBMCs, and that stimulation of HRECs with cell-free supernatants of PHA-activated PBMCs results in a decrease in the abundance of miR-30a-3p (P=0.02) (FIG. 6). As expected, activation of HRECs with cell-free supernatants of PHA-activated PBMCs increased the expression of mRNA-encoding proinflammatory cytokines MCP-1, RANTES, and IP-10 in HRECs (FIG. 7).

Example 6

Renal Allograft Recipients and Biopsy Specimens.

We investigated microRNA expression patterns of 33 renal allograft biopsies obtained from 32 adult recipients of human renal allografts: 12 biopsies from 11 recipients with graft dysfunction [mean (±SD) creatinine: 5.6±3.5 mg/dL] and biopsy-confirmed AR according to the Banff 97 classification [mean age (±SD): 38.5±8.6 yr, 7 men and 4 women, 5 living and 6 deceased donors] and 21 biopsies from 21 recipients with stable allograft function (creatinine: 1.3±0.3 mg/dL) and normal allograft biopsy (46.4±11.5 yr, 8 men and 13 women, 15 living and 6 deceased donors). The mean (±SE) time to biopsy was 19.1±7.0 months posttransplantation in the AR group and 6.3±0.9 months in the group with stable graft function and normal biopsy results (P=0.51, Maim-Whitney test). Additional information of the study subjects is given in Table 1 and in the discussion below.

Example 7

MicroRNA Expression Profiling. Global miRNA profiling of allograft biopsy specimens was studied using the TaqMan low-density array human microRNA panel v1.0 containing 365 mature human miRNAs (Applied Biosystems). miR-NAs found to be differentially expressed in AR biopsies compared to normal allograft biopsies were quantified using TaqMan miRNA assays (Applied Biosystems) modified by the incorporation of our standard curve protocol. Details for total RNA purification, miRNA profiling, quantification, and data analysis are provided below.

Example 8

Measurement of Intragraft Levels of mRNA Using Kinetic Quantitative PCR Assay.

The expression level of mRNAs was quantified using real-time quantitative PCR assays as detailed below. Primers and probes sequences are shown in Table 4, below.

TABLE 4

Oligonucleotide primers and probes used in real-time quantitative polymerase chain reaction assays for the quantification of mRNAs

| Gene | Accession number | Sequence | Location |
|---|---|---|---|
| CD3-epsilon | NM_000733 | Sense: 5'-AAGAAATGGGTGGTATTACACAGACA-3' (SEQ ID NO: 54) | 131-156 |
| | | Antisense: 5'-TGCCATAGTATTTCAGATCCAGGAT-3' (SEQ ID NO: 55) | 233-209 |
| | | Probe: 5'-FAM-CCATCTCTGGAACCACAGTAATATTGACATGCC-TAMRA-3' (SEQ ID NO: 56) | 170-202 |
| CD20 | NM_021950 | Sense: 5'-AACTCCCCATCTACCCAATACTGTT-3' (SEQ ID NO: 57) | 616-640 |
| | | Antisense: 5'-AGAAGGCAAAGATCAGCATCACT-3' (SEQ ID NO: 58) | 697-675 |
| | | Probe: 5'-FAM-CAGCATACAATCTCTGTTCTTGGGCATTTTG-TAMRA-3' (SEQ ID NO: 59) | 642-672 |
| NKCC-2 | BC040138.2 | Sense: 5'-TCACGAGCAACTCGCAAAGA-3' (SEQ ID NO: 60) | 588-607 |
| | | Antisense: 5'-TCCCATCACCGTTAGCAACTC-3' (SEQ ID NO: 61) | 658-638 |
| | | Probe: 5'-FAM-TGTGGCAGTCACCCCAAGTTCAGC-TAMRA-3' (SEQ ID NO: 62) | 609-632 |
| USAG-1 | NM_015464 | Sense: 5'-TGGAGGCAGGCATTTCAGTAA-3' (SEQ ID NO: 63) | 364-366 |
| | | Antisense: 5'-TTCCCGGCAACCCACTT-3' (SEQ ID NO: 64) | 412-396 |
| | | Probe: 5'-FAM-CCCGAGTGTTCCGATCCAGTCCAGT-TAMRA-3' (SEQ ID NO: 65) | 392-368 |
| H-ras | NM_001130442.1 | Sense 5'-TGTGTGTGTTTGCCATCAACA-3' (SEQ ID NO: 66) | 424-444 |
| | | Antisense: 5'-CGTTTGATCTGCTCCCTGTACTG-3' (SEQ ID NO: 67) | 493-471 |
| | | Probe: 5'-FAM -CACCAAGTCTTTTGAGGAC-MGB-3' (SEQ ID NO: 68) | 446-464 |
| c-myc | NM_002764.3 | Sense 5'-ACACCGCCCACCACCAG-3' (SEQ ID NO: 69) | 1299-1315 |
| | | Antisense: 5'-TCCACAGAAACAACATCGATTTCT-3' (SEQ ID NO: 70) | 1349-1372 |
| | | Probe: 5'-FAM AGGAACAAGAAGATGAGG-MGB-3' (SEQ ID NO: 71) | 1330-1347 |
| MCP-1 | NM_002982.2 | Sense: 5'-CATAGCAGCCACCTTCATTCC-3' (SEQ ID NO: 72) | 107-127 |
| | | Antisense: 5'-TCTGCACTGAGATCTTCCTATTGG-3' (SEQ ID NO: 73) | 210-186 |
| | | 5'-FAM-CAGATGCAATCAATGCCCCAGTCACC-TAMRA-3' (SEQ ID NO: 74) | 145-170 |
| RANTES | NM_002985.2 | Sense: 5'-TCTGCGCTCCTGCATCTG-3' (SEQ ID NO: 75) | 118-135 |
| | | Antisense: 5'-AGTGGGCGGGCAATGTAG-3' (SEQ ID NO: 76) | 193-176 |
| | | Probe: 5'-FAM-TCGGACACCACACCCTGCTGCT-TAMRA-3' (SEQ ID NO: 77) | 150-171 |
| IP-10 | NM_001565.1 | Sense: 5'-TGTCCACGTGTTGAGATCATTG-3' (SEQ ID NO: 78) | 235-256 |
| | | Antisense: 5'-GGCCTTCGATTCTGGATTCA-3' (SEQ ID NO: 79) | 309-290 |
| | | Probe: 5'-FAM-TACAATGAAAAAGAAGGGTGAGAA-MGB-3' (SEQ ID NO: 80) | 258-281 |
| 18S rRNA | K03432 | Sense: 5'-GCCCGAAGCGTTTACTTTGA-3' (SEQ ID NO: 81) | 929-948 |
| | | Antisense: 5'-TCCATTATTCCTAGCTGCGGTATC-3' (SEQ ID NO: 82) | 1009-986 |
| | | Probe: 5'-FAM-AAAGCAGGCCCGAGCCGCC-TAMRA-3' (SEQ ID NO: 83) | 965-983 |

Example 9

Cell Culture. The procedures for the in vitro studies using peripheral blood mononuclear cells and normal human renal epithelial cells are described below.

Example 10

Human Renal Allograft Biopsy Classification. Percutaneous core needle biopsies were obtained and formalin-fixed, paraffin embedded renal biopsies were stained with hematoxylin and eosin, periodic acid-Schiff and Masson's trichrome, and analyzed by a pathologist, blinded to the results of molecular studies using the Banff 97 classification. Immunosuppression consisted of a calcineurin inhibitor-based regimen, with methyl prednisolone for the initial treatment of acute rejection. The study was approved by the Institutional Review Board at the Weill Cornell Medical College, and each patient gave written informed consent.

Example 11

Global MicroRNA Expression Profiling. Allograft biopsy samples were placed in RNAlater (Ambion) and stored at −80° C. until RNA extraction. Total RNA was extracted from biopsies using the mirVana miRNA isolation kit according to the manufacturer's specification (Ambion). The yield and purity of RNA were measured using a NanoDrop ND-1000 spectrophotometer (Nanodrop Technologies), and RNA integrity was assessed using the RNA 6000 Nano LabChip kit (Agilent Technologies). We used the TaqMan Low-Density Array Human MicroRNA Panel v1.0 (Applied Biosystems), a 384-well microfluidic card that contains primers and probes for 365 different human miRNAs in addition to 2 small nucleolar RNAs that function as endogenous controls for data normalization, for global miRNA profiling of allograft biopsy specimens. Three acute rejection (AR) biopsy samples and 4 normal kidney allograft biopsy specimens were profiled for global miRNA gene expression patterns (7 biopsies, training set). Total RNA (480 ng) was reverse transcribed using the TaqMan Multiplex RT set for TaqMan Array Human MicroRNA Panel v1.0. Each RT reaction was diluted 62.5-fold with water, and 55 µL of each diluted product was combined with 55 µL of TaqMan 2× Universal PCR Master Mix, No AmpErase UNG. One-hundred microliters of the sample/master mix for each Multiplex pool were loaded into fill reservoirs of the microfluidic card; the array was then centrifuged and mechanically sealed with the Applied Biosystems sealer device. Quantitative PCR was carried out on an Applied BioSystems 7900HT thermocycler using the manufacturer's recommended cycling conditions. Fold changes for each miRNA were normalized to the endogenous control RNU44 small nucleolar RNA. The relative expression levels between samples were calculated using the comparative delta $C_T$ (threshold cycle number) method with a control sample (normal) as the reference point.

Example 12

TaqMan Low-Density Array Analysis. Data analysis was performed by using the SDS software version 2.3 and the baseline and threshold were automatically set. Data were normalized and then analyzed to define genes that are differentially expressed between the AR biopsies and normal protocol biopsies. Assays that had $C_T$ values>35 were removed from the analysis. The delta $C_T$ values were calculated by using RNU44 as the endogenous control. Unsupervised clustering method and principal component analysis (PCA) were used to visualize patterns in the data set without any a priori sample classification. Average linkage clustering analysis was implemented in the Cluster program and Java Tree View 1.0 .12 software. PCA were done using the xlstat software. Data were analyzed using Applied Biosystem's ABqPCR data analysis tool (Applied Biosystems, personal communication). A Student t test was performed to detect differentially expressed miRNAs between the AR samples and normal allograft biopsies.

Example 13

Quantification of MicroRNAs. miRNAs found to be differentially expressed in AR biopsies compared to normal allograft biopsies by the TaqMan Low-Density Array were measured using Taq-Man miRNA assays (Applied Biosystems) in 9 additional AR samples and 17 additional normal allograft biopsies (26 biopsies, validation set). TaqMan miRNA assays were also used to quantify miRNA in the in vitro experiments. Reverse transcription for individual miRNAs was performed using the TaqMan microRNA reverse transcription kit (Applied Biosystems). Briefly, cDNA were reverse transcribed from total RNA samples using specific miRNA primers from the TaqMan microRNA assays (Applied Biosystems) and reagents from the TaqMan microRNA reverse transcription kit (Applied Biosystems). Each reverse transcription reaction consists of 7 µL master mix, 3 µL miRNA-specific primer, and 5 µL of 1 ng/µL dilution of total RNA. Reverse transcription was done in Veriti thermal cyclers (Applied Biosystems), using the following parameter values: 16° C. for 30 min, 42° C. for 30 min, and 85° C. for 5 min. PCR products were amplified from cDNA samples using the TaqMan microRNA assay (Applied Biosystems). PCR for each sample was set up in duplicate as a 20-µL reaction volume using 1 µL 20X TaqMan miRNA assay (Applied Biosystems) containing a mix of miRNA-specific forward PCR primer, a specific reverse PCR primer, and a miRNA-specific TaqMan MGB probe, TaqMan Universal PCR Master Mix, and 1.5 µL cDNA. A synthetic amplicon was used to develop a standard curve (see below) and TaqMan $C_T$ values were converted into absolute copy numbers. See, N Engl J Med 358:353-361. miRNA copy numbers were normalized using RNU44 small nucleolar RNA copy numbers and the abundance of miRNAs was expressed as a ratio of miRNA copies to RNU44 copies (miRNA copies in 1 µg RNA/RNU44 small nucleolar RNA copies in 1 µg RNA). TaqMan microRNA assays were performed using an ABI Prism 7500 real-time PCR system.

Example 14

Quantification of Messenger RNAs. Levels of mRNAs were measured using an ABI Prism 7500 Fast detection system (Applied Biosystems). PCR for each sample was set up in duplicate as a 20-µL reaction volume using 10 µL TaqMan Universal PCR Master Mix, 2.5 µL preamplified template cDNA, 0.15 µL primers (sense primer and antisense primer, 50 µM each; Table 4 lists the oligonucleotide primers and probes), 0.05 µL probe (100 µM), and 7.34 µL of water. The PCR amplification protocol consists of an initial hold at 95° C. for 20 seconds and 40 cycles of denaturing at 95° C. for 3 seconds and primer annealing and extension at 60° C. for 30 seconds. Transcript levels are calculated using our standard curve method (see below), and mRNA copy numbers are normalized using 18S rRNA copy numbers (mRNA copies in 1 μg RNA/18S rRNA copies in 1 ng RNA).

Example 15

Method for Absolute Quantification of mRNAs and miRNAs. RNA levels (mRNA and miRNA) were calculated using our previously described standard curve method, incorporated by reference herein from Kawai T, et al. (2008) HLA-mismatched renal transplantation without maintenance immunosuppression. N Engl J Med 358:353-361. The standard curve was established using PCR generated 73-bp mouse Bak amplicon as the standard. The Bak amplicon was generated in a PCR using GeneAmp 9600 thermal cycler and with 3 μL cDNA and 22 μL of dNTP, 10μ PCR buffer, TaqDNA polymerase, and Bakspecific oligonucleotide primer pair [sense primer: 5' CCCACATCTGGAGCAGAGTCA 3' (192-212) (SEQ ID NO:84); antisense primer: 5' CAGATGCCATTTTTCAGGTCTTG 3' (264-242) (SEQ ID NO:85), accession no. Y13231]. The PCR product was separated by electrophoresis with a 2% agarose gel and the amplicon size (73 bp) was confirmed using a DNA size standard of pUC mix marker 8 (Crystalgen). The Bak amplicon was isolated and purified from the gel with QIAquick gel extraction kit (QIAGEN). The absolute quantity of the purified amplicon was measured by A260 and converted to the number of copies using the molecular weight of DNA. The Bak amplicon was diluted to the concentration of $10^7$ copies/μL (stock solution). When a standard curve was to be established for the real-time quantitative PCR assay, the stock solution was diluted over 6 orders of magnitude (1,000,000, 100,000, 10,000, 1,000, 100, and 10 copies per 1 μL) (work solution). Work solution (2.5 μL) was added to duplicate wells and amplified with Bak-specific primer pair and Bakspecific fluorogenic TaqMan probe [5' FAM CAGTGACAAGTGACGGTGGTCTCCA TAMRA 3' (215-240) (SEQ ID NO:86)]. The threshold cycles ($C_T$) were then plotted vs. the log of the initial amount of the Bak amplicon to develop the standard curve. The thresholds were in the exponential phase of the PCR and the higher the initial copy number of the Bak amplicon, the lower was the $C_T$ value.

Example 16

Isolation of Normal Human Peripheral Blood Mononuclear Cells and Activation with Phytohaemagglutinin. Peripheral blood mononuclear cells (PBMCs) were obtained from whole blood of 7 healthy volunteers by standard Ficoll density-gradient centrifugation. PBMCs were resuspended at $10^6$ cells/mL in RPMI 1640 (Gibco BRL) containing 5% (vol/vol) heat-inactivated FCS, penicillin (100 U/mL), streptomycin sulfate (100 μg/mL), and L-glutamine (4 mM). The PBMCs ($10^6$/mL) were incubated without or with phytohaemagglutinin (PHA) (Remel) at a final concentration of 2 μg/mL. Following incubation for 24, 48, or 72 h at 37° C. in 5% $CO_2$ humidified atmosphere, the cells were retrieved, washed twice with PBS, and pelleted by centrifugation. Six hundred microliters of lysis/binding buffer from the mirVana miRNA isolation kit (Ambion) were added directly to the cell pellet. Lysates were stored at −80° C. or total RNA was immediately extracted using the manufacturer's recommended protocol for total RNA isolation. Cell-free supernatants of PBMCs incubated without or with 2 μg/mL PHA were collected by centrifugation and concentrated (Amicon, Millipore) for the in vitro studies using human renal epithelial cells.

Example 17

Human Renal Epithelial Cells Culture. Normal human renal tubular epithelial cells (HRECs) were harvested from human nephrectomy specimens removed for renal cell carcinoma and isolated according to previously published methods, with minor modifications. Fragments of nontumoral renal cortex were minced and digested with collagenase IV (250 IU/mL) for 3 h at 37° C. Cells were centrifuged and the pellets washed 3 times with PBS. Cells were then cultured in Dulbecco's modified Eagle medium (DMEM) containing 5 μg/mL insulin, 10 μg/mL human apotransferrin, 500 ng/mL hydrocortisone, 10 ng/mL EGF, 6.5 ng/mL triiodothyronin, 5 ng/mL sodium selenite, 1% FCS, 25 IU/mL penicillin, 25 μg/mL streptomycin, and 10 mM Hepes buffer. HRECs were then incubated at 37° C. in 5% $CO_2$ and 95% air. The characterization of our cellular model has been published previously, confirming the proximal descent of the vast majority of the cultured tubular epithelial cells. Experiments were not performed with HRECs beyond the third passage. HRECs were harvested at 80% confluence and seeded in 60-mm dishes at $3 \times 10^5$ cells/dish. At 50% confluence, cells were treated with various amounts of concentrated cell-free supernatants of PBMCs incubated without or with 2 μg/mL PHA. Following 24 or 48 h of culture at 37° C. in 5% CO2-95% air-humidified atmosphere, the HRECs were retrieved and washed twice with PBS. Six hundred microliters of lysis/binding buffer from the mirVana miRNA isolation kit (Ambion) were added directly to the culture plate to lyse the cells. Lysates were harvested manually with a sterile cell scraper and transferred to a 1.5-mL tube. Samples were stored at −80° C. or RNA was immediately extracted using the manufacturer's recommended protocol for total RNA isolation.

Example 18

Statistical Analysis. We used a conventional receiver-operating characteristic (ROC) curve to analyze mRNA and miRNA levels to determine the cutoff points that yielded the highest combined sensitivity and specificity with respect to distinguishing subjects with acute rejection from subjects with stable graft function and normal biopsy results. We calculated the area under the curve (AUC) and 95% confidence intervals for the AUC. The association between intragraft levels of mRNAs and miRNAs was analyzed using the Pearson regression, and the relationship between intragraft levels of miRNA or mRNA and renal allograft function was also analyzed using the Pearson regression. All data were expressed as mean±SE, unless otherwise specified. Statistical significance was tested by Student's t test or paired t test.

Example 19

Based on the above disclosure, we identified that intragraft miRNA profiles distinguish patients with AR of human allografts from patients with normal allograft biopsy results, and that AR can be diagnosed with a high degree of accuracy with the use of intragraft levels of miRNAs. Moreover, miRNA profiles were also predictive of renal allograft function. Our observations, together, support the hypothesis that intragraft miRNA expression patterns may serve as biomarkers of human renal allograft status.

Figure 1:
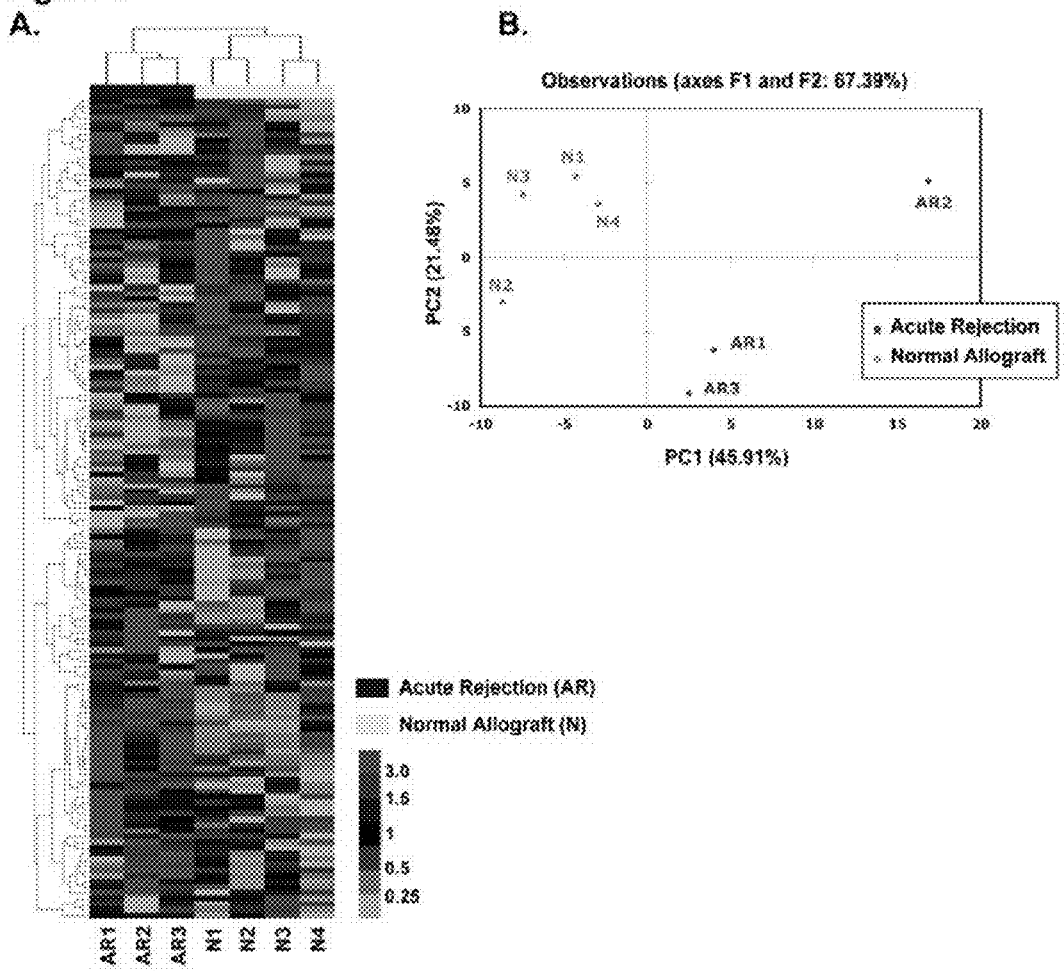
FIG. 1. Unsupervised hierarchical clustering and principal component analysis of miRNA expression profiles differentiate acute rejection biopsies from normal allograft biopsies of human renal allografts. (A) MicroRNA (miRNA) expression patterns of 7 human kidney allograft biopsies [3 showing histological features of acute rejection (AR) and 4 with normal allograft biopsy results (N)] were examined using microfluidic cards containing TaqMan probes and primer pairs for 365 human mature miRNAs. A total of 174±7 miRNAs were expressed at a significant level (i.e., $C_T$<35) in all samples. Gender, age, ethnicity, type of transplantation, and time from transplantation to biopsy were as follow: AR1 (Male, Black, 52 years, living donor, 161 days), AR2 (male, White, 32 years, living donor, 119 days), AR3 (Female, White, 48 years, deceased donor, 31 days), N1 (female, Black, 40 years, living donor, 203 days), N2 (Male, Indian, 50 years, living donor, 191 days), N3 (Male, Black, 31 years, living donor, 196 days), and N4 (Male, Asian, 51 years, deceased donor, 88 days). The biopsies were grouped by unsupervised hierarchical clustering on the basis of similarity in expression patterns. The degree of relatedness of the expression patterns in biopsy samples is represented by the dendrogram at the top of the panel. Branch lengths represent the degree of similarity between individual samples (Top) or miRNA (Left). Two major clusters (Top) accurately divided AR biopsies from normal allograft biopsies. Each column corresponds to the expression profile of a renal allograft biopsy, and each row corresponds to a miRNA. The color in each cell reflects the level of expression of the corresponding miRNA in the corresponding sample, relative to its mean level of expression in the entire set of biopsy samples. The increasing intensities of red mean that a specific miRNA has a higher expression in the given sample and the increasing intensities of green mean that this miRNA has a lower expression. The scale (Bottom Right) reflects miRNA abundance ratio in a given sample relative to the mean level for all samples. (B) Principal component analysis of 7 kidney allograft biopsies based on the expression of 174 small RNAs significantly expressed (i.e., $C_T$<35) in all of the samples. PCA is a bilinear decomposition method designed to reduce the dimensionality of multivariable systems and used for overviewing clusters within multivariate data. It transforms a number of correlated variables into a smaller number of uncorrelated variables called principal components (PC). The first PC accounts for as much of the variability in the data as possible, and each succeeding component accounts for as much of the remaining variability as possible. PCA showed evident clustering and confirmed the separation of AR samples from normal allograft biopsies. Samples were accurately grouped by PC1, which explained 45.91% of the overall miRNA expression variability, whereas PC2 explained 21.48% of variability and did not classify the samples according to their diagnosis.

We used a 2-step approach to develop miRNA signatures predictive of AR. First, we ascertained intragraft expression patterns of 365 mature human miRNAs in 7 human renal allograft biopsies classified as AR or normal. Global expression profiling identified miRNAs differentially expressed in AR biopsies compared to normal biopsies (FIGS. 1 and 2). In the second step, with the use of modified TaqMan miRNA assays, we determined absolute copy numbers of miRNAs in 26 additional renal allograft biopsies (FIG. 3). Our approach resolved that intragraft levels of miR-142-5p, -155, -223, -10b, -30a-3p, and let-7c are diagnostic of AR, with miR-142-5p, miR-155, and miR-223 each predicting AR with >90% sensitivity and specificity (Table 1). Intragraft levels of mRNA for CD3, CD20, NKCC-2, and USAG-1 were also diagnostic of AR, but with less combined sensitivity and specificity.

Intragraft levels of miR-142-5p, -155, -223, -10b, -30a-3p, and let-7c predicted renal graft function with miR-142-5p and miR-10b showing the strongest association with graft function. Among the mRNAs analyzed, mRNA for CD3, but not mRNAs for CD20, NKCC-2, and USAG-1, predicted graft function, and the association between CD3 mRNA and graft function was weaker compared to that of miR-142-5p or miR-10b. Our observations that intragraft miRNA expression patterns are predictive of allograft status, in addition to the existing data that miRNAs are stable, present in high abundance, and can be examined in formalin-fixed tissues, advance the idea that miRNA expression patterns may be of value as biomarkers in clinical transplantation.

Several of the miRNAs found at a higher level in AR biopsies compared to normal allograft biopsies may play an important role in innate and adaptive immunity. Our in vitro studies showed that activation with the polyclonal T-cell mitogen PHA increases miR-155 expression in normal human PBMCs.

Intragraft levels of miR-146 were higher in AR samples compared to normal allograft biopsies. miR-146 is expressed at low levels in naïve T cells, is upregulated in Th1 cells, but not in Th2 cells, and is considered as a Th1-specific miRNA. In support of Th1-type cells infiltrating rejecting human renal allografts, we found that intragraft level of mRNA for the type 1 cytokine IFN-γ but not the level of mRNA for the Th2 cytokine IL-4 were higher in AR biopsies compared to normal allograft biopsies (FIG. 8).

Among the miRNAs overexpressed in the AR biopsies, miR-223 levels were the highest. We also found the abundance of miR-223 to be higher compared to that of miR-142-5p or miR-155 in normal human PBMCs, and that activation of PBMCs with PHA results in a reduction of miR-223 expression.

Intragraft levels of miR-142 were also higher in AR biopsies compared to normal allograft biopsies. We found that activation results in a reduction, albeit not statistically significant (P=0.08), in the expression of miR-142 in PBMCs.

Acute rejection of human renal allografts was also characterized by underexpression of miRNAs within the rejecting allografts compared to allografts with normal biopsy results. Indeed, among the 53 miRNAs differentially expressed between AR biopsies and normal biopsies, 43 were underexpressed and only 10 were overexpressed in the AR biopsies (FIG. 2).

Two members of the let-7 family (let-7a and let-7c) were underexpressed in AR biopsies. Our investigation showed that let-7c is downregulated in PHA-activated PBMCs (FIGS. 5 D and E) and mRNA for both H-ras and c-myc are upregulated (FIG. 5 F-I). However, the reduction in the expression of let-7c was not observed 24 h after activation and was evident after 48 h, whereas the maximum upregulation of H-ras and c-myc was observed 24 h following activation (FIGS. 5 H and I). Thus, downregulation of let-7c does not appear to be an absolute prerequisite for the upregulation of H-ras or c-myc in normal human PBMCs.

miR-30a-3p and miR-10b were both underexpressed in AR biopsies compared to normal allograft biopsies (FIG. 3). These miRNAs were expressed at a greater abundance in HRECs compared to PBMCs, and activation of HRECs, as demonstrated by increased expression of mRNA for proinflammatory chemokines MCP-1, RANTES, and 1P-10 (FIG. 7), was associated with a reduced expression of miR-30a-3p (FIG. 6).

Example 20

Urinary Cell Levels of miRNA 155 are diagnostic of acute rejection. Total RNA containing miRNAs was isolated from urinary cells collected from renal allograft recipients and levels of RNU44 (house keeping gene) and miRNA 155 were measured real time quantitative PCR assays. Urinary cell levels of miRNA 155 and not RNU 44 were significantly higher in urine from patients whose biopsies were classified acute rejection (n=3 specimens) compared to urine from patients with stable graft function and normal biopsy findings (n=13 specimens).

TABLE 1

Characteristics of renal allograft recipients*

| Biopsy ID | Sample group | Recipient gender | Ethnicity | Recipient age (years) | Date of transplantation | Type of transplantation | Date of biopsy (days) | Indication of biopsy | Immunosuppressive treatment at biopsy† |
|---|---|---|---|---|---|---|---|---|---|
| #1 | Training set | M | Black | 52 | Jul. 08, 2004 | Living | 161 | Graft dysfunction | Tacrolimus/MMF/ steroids |
| #2 | Training set | M | White | 32 | Jan. 11, 2007 | Living | 119 | Graft dysfunction | Tacrolimus/MMF |
| #3 | Training set | F | White | 48 | Mar. 04, 2007 | Deceased | 31 | Graft dysfunction | Tacrolimus/MMF/ steroids |
| #4 | Training set | F | Black | 40 | Jun. 19, 2003 | Living | 203 | Protocol | Tacrolimus/MMF |
| #5 | Training set | M | Indian | 50 | Jul. 05, 2005 | Living | 191 | Protocol | Tacrolimus/MMF |
| #6 | Training set | M | Black | 31 | May 06, 2004 | Living | 196 | Protocol | Tacrolimus/MMF |
| #7 | Training set | M | Asian | 51 | Mar. 24, 2005 | Deceased | 88 | Protocol | Tacrolimus/MMF |
| #8 | Validation set | M | White | 36 | Nov. 24, 2002 | Deceased | 1081 | Graft dysfunction | Tacrolimus/MMF/ steroids |
| #9 | Validation set | M | Black | 48 | Jan. 15, 2006 | Deceased | 166 | Graft dysfunction | Tacrolimus/MMF/ steroids |
| #10 | Validation set | F | Hispanic | 28 | Feb. 27, 2001 | Living | 1511 | Graft dysfunction | Tacrolimus/MMF/ steroids |

TABLE 1-continued

Characteristics of renal allograft recipients*

| | | | | | | | | | |
|---|---|---|---|---|---|---|---|---|---|
| #11 | Validation set | M | White | 36 | Nov. 24, 2002 | Deceased | 969 | Graft dysfunction | Tacrolimus/MMF/steroids |
| #12 | Validation set | M | Black | 37 | Jan. 19, 2006 | Living | 244 | Graft dysfunction | Non compliant |
| #13 | Validation set | F | Hispanic | 58 | May 09, 2002 | Living | 370 | Protocol | Tacrolimus/MMF |
| #14 | Validation set | M | Hispanic | 61 | Jun. 30, 2005 | Living | 35 | Protocol | Tacrolimus/MMF |
| #15 | Validation set | M | White | 67 | Aug. 26, 2005 | Deceased | 40 | Protocol | Tacrolimus/MMF |
| #16 | Validation set | F | White | 57 | Mar. 17, 2005 | Living | 175 | Protocol | Tacrolimus/MMF/steroids |
| #17 | Validation set | F | Black | 44 | Nov. 06, 2003 | Living | 189 | Protocol | Tacrolimus/MMF |
| #18 | Validation set | F | Black | 63 | May 24, 2005 | Deceased | 86 | Protocol | Tacrolimus/MMF |
| #19 | Validation set | F | White | 58 | Mar. 11, 2005 | Living | 404 | Protocol | Tacrolimus/MMF/steroids |
| #20 | Validation set | M | White | 47 | Dec. 14, 2004 | Living | 366 | Protocol | Tacrolimus/MMF |
| #21 | Validation set | F | Black | 51 | Mar. 24, 2006 | Living | 40 | Protocol | Tacrolimus/MMF |
| #22 | Validation set | F | Other | 43 | Dec. 02, 2004 | Deceased | 147 | Graft dysfunction | Tacrolimus/MMF/steroids |
| #23 | Validation set | F | Black | 24 | Jul. 08, 1999 | Deceased | 2283 | Graft dysfunction | Tacrolimus/MMF/steroids |
| #24 | Validation set | M | Black | 44 | Mar. 25, 2005 | Deceased | 137 | Graft dysfunction | Tacrolimus/MMF/steroids |
| #25 | Validation set | M | Hispanic | 34 | Nov. 01, 2005 | Living | 20 | Graft dysfunction | Tacrolimus/MMF |
| #26 | Validation set | F | Hispanic | 37 | Jan. 16, 2003 | Living | 145 | Protocol | Tacrolimus/MMF/steroids |
| #27 | Validation set | F | Black | 27 | Sep. 17, 2002 | Living | 365 | Protocol | Tacrolimus/MMF/steroids |
| #28 | Validation set | M | White | 46 | Jun. 03, 2003 | Living | 408 | Protocol | Tacrolimus/MMF |
| #29 | Validation set | M | Asian | 33 | Oct. 15, 2003 | Deceased | 201 | Protocol | Tacrolimus/MMF/steroids |
| #30 | Validation set | F | Black | 35 | Oct. 23, 2005 | Deceased | 221 | Protocol | Tacrolimus/MMF |
| #31 | Validation set | F | Hispanic | 32 | Jan. 25, 2005 | Living | 79 | Protocol | Tacrolimus/MMF |
| #32 | Validation set | F | Asian | 44 | Jan. 14, 2005 | Living | 109 | Protocol | Tacrolimus/MMF/steroids |
| #33 | Validation set | F | White | 43 | Mar. 22, 2005 | Living | 30 | Protocol | Tacrolimus/MMF |

| Biopsy ID | Banff 97 diagnostic cathegory‡ | Banff grade | C4d staining§ | Tacrolimus blood level at biopsy (ng/mL) | Serum creatinine (mg/dL) | | |
|---|---|---|---|---|---|---|---|
| | | | | | Baseline level | At biopsy | After treatment of acute rejection |
| #1 | 4 | IB | Neg | 4.0 | 1.1 | 3.2 | 2.4 |
| #2 | 4 | IB | Neg | 13.1 | 1.6 | 10.2 | 2.3 |
| #3 | 4 | IB | Neg | 7.0 | 2.2 | 3.3 | 1.7 |
| #4 | 1 | | — | 7.5 | 1.1 | 1.3 | — |
| #5 | 1 | | — | 6.2 | 1.4 | 1.7 | — |
| #6 | 1 | | — | 8.7 | 1.2 | 1.7 | — |
| #7 | 1 | | — | 13.1 | 1.3 | 1.3 | — |
| #8 | 4 | IB | Neg | 6.1 | 1.9 | 4.1 | 3.3 |
| #9 | 4 | IB | Neg | 1.7 | 2.7 | 6.7 | 3.9 |
| #10 | 4 | IB | — | 7.2 | 1.3 | 10.4 | HD¶ |
| #11 | 4 | IB | Neg | 6.2 | 1.2 | 2.8 | 1.9 |
| #12 | 4 | IB | Neg | <1.5 | 1.9 | 7.9 | 3.5 |
| #13 | 1 | | — | 2.0 | 1.0 | 1.0 | — |
| #14 | 1 | | — | 9.4 | 1.2 | 1.2 | — |
| #15 | 1 | | — | 13.5 | 1.2 | 1.7 | — |
| #16 | 1 | | — | 10.3 | 1.3 | 1.4 | — |
| #17 | 1 | | — | — | 1.4 | 1.4 | — |
| #18 | 1 | | — | 9.9 | 1.2 | 1.3 | — |
| #19 | 1 | | — | 7.4 | 1.3 | 1.7 | — |
| #20 | 1 | | — | 7.3 | 1.6 | 1.6 | — |
| #21 | 1 | | — | 8.0 | 1.1 | 1.1 | — |
| #22 | 4 | IB | Focal | 8.8 | 0.9 | 1.8 | 1.0 |
| #23 | 4 | IB | Neg | 5.1 | 1.6 | 11.2 | HD |
| #24 | 4 | IB | Neg | 3.1 | 2.2 | 3.8 | 2.6 |
| #25 | 4 | IA | Neg | 12.9 | 1.3 | 2.1 | 1.3 |
| #26 | 1 | | — | 4.7 | 0.9 | 0.9 | — |
| #27 | 1 | | — | 10.9 | 0.9 | 0.9 | — |
| #28 | 1 | | — | 6.9 | 1.2 | 1.4 | — |
| #29 | 1 | | — | 8.5 | 1.4 | 1.5 | — |
| #30 | 1 | | — | 6.7 | 1.2 | 1.3 | — |
| #31 | 1 | | — | 10.9 | 0.9 | 1.2 | — |
| #32 | 1 | | — | 5.3 | 1.0 | 1.2 | — |
| #33 | 1 | | — | 12.1 | 0.7 | 1.0 | — |

INCORPORATION OF SEQUENCE LISTING:

Incorporated herein by reference in its entirety is the Sequence Listing for the application. The Sequence Listing is disclosed on a computer-readable ASCII text file entitled, "Sequence_Listing_955_88PCTUS.txt", created on Sep. 13, 2011. The sequence.txt file is 18 KB in size.

What is claimed is:

1. A method comprising:
   (a) measuring expression of one or a combination of small non-coding marker RNAs in a sample comprising kidney, blood, and/or urine from a patient by quantitative polymerase chain reaction to generate a measured amount of expression, wherein said one or a combination of small non-coding marker RNA(s) is selected from the group of SEQ. ID NOs: 1-9 and 50;
   b) quantifying a difference between the measured amount of expression in step (a) and a reference amount of expression of said one or a combination of small non-coding marker RNAs in a person having a non-rejected organ or a second biological sample from the patient; and
   (c) administering an anti-rejection treatment to the patient to reduce a risk of kidney transplant rejection when an increase of expression of at least two-fold is detected of said small non-coding marker RNA(s) in the sample compared to said reference amount.

2. The method according to claim 1, wherein the small non-coding marker RNA is miR-142-5p CAUAAAGUAGAAAGCACUAC (SEQ ID NO:1).

3. The method according to claim 1, wherein the small non-coding marker RNA is miR-142-3p UGUAGUGUUUCCUACUUUAUGGA (SEQ ID NO:2).

4. The method according to claim 1, wherein the small non-coding marker RNA is miR-155 UUAAUGCUAAUCGUGAUAGGGG (SEQ ID) NO:3).

5. The method according to claim 1, wherein the small non-coding marker RNA is miR-146a UGAGAACUGAAUUCCAUGGGUU (SEQ ID NO:4).

6. The method according to claim 1, wherein the small non-coding marker RNA is miR-146b UGAGAACUGAAUUCCAUAGGCU (SEQ ID NO:5).

7. The method according to claim 1, wherein the small non-coding marker RNA is miR-342 UCUCACACAGAAAUCGCACCCGUC (SEQ ID NO:6).

8. The method according to claim 1, wherein the small non-coding marker RNA is miR-650 AGGAGGCAGCGCUCUCAGGAC (SEQ ID NO:7).

9. The method according to claim 1, wherein the small non-coding marker RNA is miR-21 UAGCUUAUCAGACUGAUGUUGA (SEQ ID NO:8).

10. The method according to claim 1, wherein the small non-coding marker RNA is miR-425-5p AAUGACACGAUCACUCCCGUUGA (SEQ ID NO:9).

11. The method according to claim 1, wherein the small non-coding marker RNA is miR 223 UGUCAGUUUGUCAAAUACCCC (SEQ ID NO:50).

12. The method according to claim 1, wherein the sample comprises a urine sample.

13. The method according to claim 1, wherein said reference amount is obtained by measuring an amount of expression of the small non-coding marker RNA(s) in a person having a non-rejected organ.

14. The method according to 1, wherein said reference amount is obtained by measuring an amount of expression of said small non-coding marker RNA in a second biological sample from the patient.

* * * * *

UNITED STATES PATENT AND TRADEMARK OFFICE
CERTIFICATE OF CORRECTION

PATENT NO. : 9,868,988 B2
APPLICATION NO. : 13/256422
DATED : January 16, 2018
INVENTOR(S) : Manikkam Suthanthiran Page 1 of 2

It is certified that error appears in the above-identified patent and that said Letters Patent is hereby corrected as shown below:

On the Title Page

In Column 2, item (56), under "Other Publications", Line 1, delete "Noninvasive" and insert --Non-invasive-- therefor In Column 2, item (56), under "Other Publications", Line 24, delete "sequences"," and insert --sequences)",-- therefor On page 2, in Column 1, item (56), under "Other Publications", Line 35, delete "Serial. No." and insert --Serial No.-- therefor On page 2, in Column 1, item (56), under "Other Publications", Line 52, delete ""Noninvasive" and insert --"Non-invasive-- therefor On page 2, in Column 2, item (56), under "Other Publications", Line 8, delete ""Noninvasive" and insert --"Non-invasive-- therefor On page 2, in Column 2, item (56), under "Other Publications", Line 11, after "Tissue", insert --Injury by Gene Profiling--

On page 2, in Column 2, item (56), under "Other Publications", Line 27, delete "mrna" and insert --mRNA-- therefor On page 2, in Column 2, item (56), under "Other Publications", Line 31, delete "Receipients"," and insert --Recipients",-- therefor On page 2, in Column 2, item (56), under "Other Publications", Line 40, delete ""Noninvasive" and insert --"Non-invasive-- therefor Signed and Sealed this
Twenty-eighth Day of April, 2020

Andrei Iancu
*Director of the United States Patent and Trademark Office*

On page 3, in Column 1, item (56), under "Other Publications", Line 12, delete "94(3). EPC" and insert --94(3) EPC-- therefor In the Claims In Column 59, Line 22, in Claim 1, delete "SEQ." and insert --SEQ-- therefor In Column 59, Line 23, in Claim 1, delete "b)" and insert --(b)-- therefor In Column 59, Line 41, in Claim 4, delete "ID)" and insert --ID-- therefor In Column 60, Line 31, in Claim 11, delete "miR 223" and insert --miR-223-- therefor In Column 60, Line 39, in Claim 14, after "to", insert --claim--